United States Patent
Kashino et al.

(10) Patent No.: US 11,602,719 B2
(45) Date of Patent: Mar. 14, 2023

(54) ULTRAFINE BUBBLE GENERATING APPARATUS AND ULTRAFINE BUBBLE GENERATING HEAD

(71) Applicant: CANON KABUSHIKI KAISHA, Tokyo (JP)

(72) Inventors: Toshio Kashino, Kanagawa (JP); Yoshiyuki Imanaka, Kanagawa (JP); Masahiko Kubota, Tokyo (JP); Akitoshi Yamada, Kanagawa (JP); Akira Yamamoto, Kanagawa (JP); Yumi Yanai, Kanagawa (JP); Teruo Ozaki, Kanagawa (JP); Hiroyuki Ishinaga, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 113 days.

(21) Appl. No.: 17/168,367

(22) Filed: Feb. 5, 2021

(65) Prior Publication Data

US 2021/0245124 A1 Aug. 12, 2021

(30) Foreign Application Priority Data

Feb. 12, 2020 (JP) .............................. JP2020-021491
Feb. 3, 2021 (JP) .............................. JP2021-016052

(51) Int. Cl.
| | |
|---|---|
| *B01F 23/23* | (2022.01) |
| *B01F 35/93* | (2022.01) |
| *B01F 23/231* | (2022.01) |
| *B01B 1/00* | (2006.01) |
| *B01F 23/2373* | (2022.01) |
| *B01F 23/237* | (2022.01) |

(Continued)

(52) U.S. Cl.
CPC ............ *B01F 35/93* (2022.01); *B01F 23/231* (2022.01); *A61L 9/015* (2013.01); *B01B 1/00* (2013.01); *B01F 23/2366* (2022.01); *B01F 23/2373* (2022.01); *B01F 23/237613* (2022.01); *B01F 2035/99* (2022.01)

(58) Field of Classification Search
CPC .............................. B01F 23/231; A61L 9/015
See application file for complete search history.

(56) References Cited

U.S. PATENT DOCUMENTS

| | | |
|---|---|---|
| 2020/0254468 A1 | 8/2020 | Kubota et al. |
| 2021/0129093 A1 | 5/2021 | Yamamoto et al. |

FOREIGN PATENT DOCUMENTS

| | | | |
|---|---|---|---|
| CN | 203482710 U | * | 3/2014 |
| EP | 3 816 117 A1 | | 5/2021 |
| JP | 2004-188246 A | | 7/2004 |

(Continued)

OTHER PUBLICATIONS

Extended European Search Report in European Application No. 21156362.2 dated Jun. 2021.
Kashino et al., U.S. Appl. No. 17/167,355, filed Feb. 4, 2021.

*Primary Examiner* — Robert A Hopkins
(74) *Attorney, Agent, or Firm* — Venable LLP

(57) ABSTRACT

Provided is a UFB generating apparatus capable of manufacturing an ozone UFB-contained liquid with high purity and quality. To this end, in the UFB generating apparatus capable of generating UFBs containing ozone by causing film boiling in ozone water, a liquid contact portion to come into contact with the ozone water is made of a material with corrosion resistance to ozone water.

27 Claims, 27 Drawing Sheets

(51) Int. Cl.
   *B01F 35/90* (2022.01)
   *A61L 9/015* (2006.01)

(56) References Cited

FOREIGN PATENT DOCUMENTS

| | | | |
|---|---|---|---|
| JP | 2019-042732 A | 3/2019 | |
| WO | 2013/065356 A1 | 5/2013 | |
| WO | 2019/044913 A1 | 3/2019 | |
| WO | WO-2019044913 A1 * | 3/2019 | ............. A01N 25/02 |

* cited by examiner

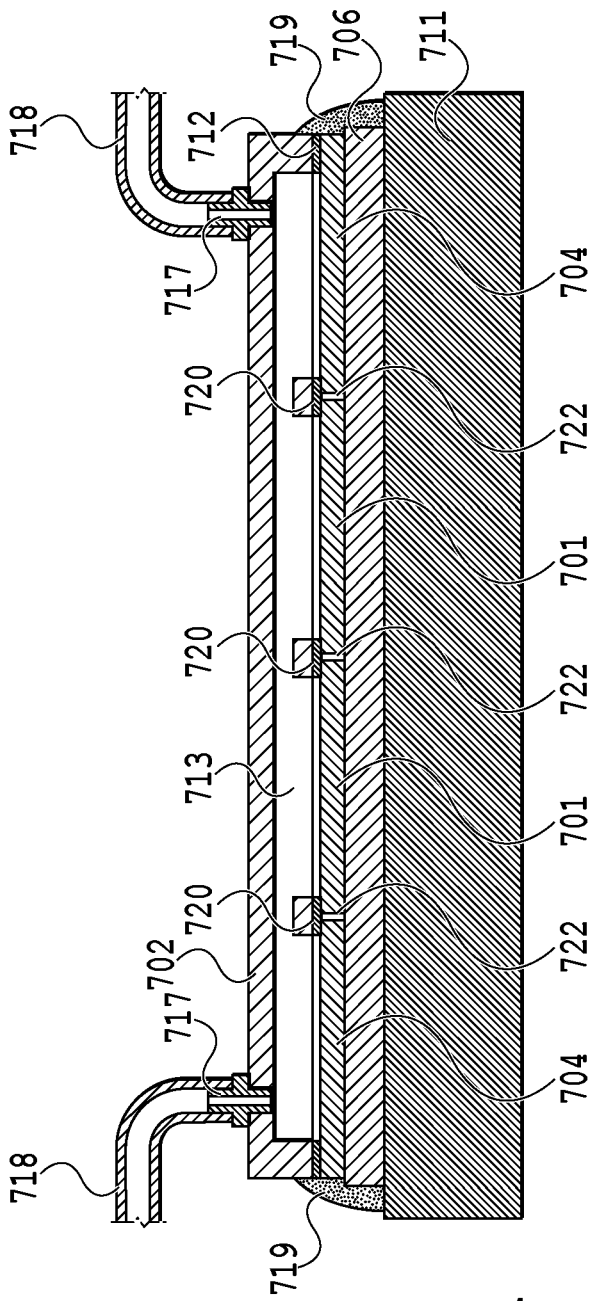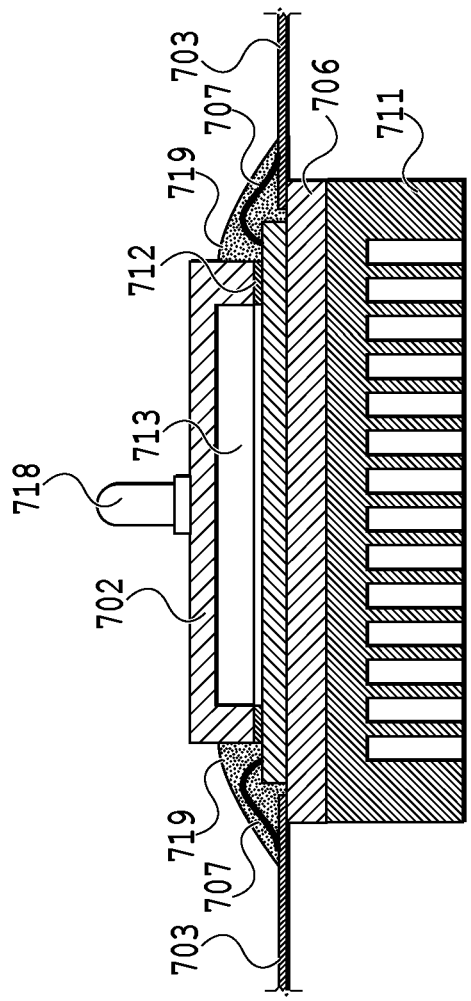
FIG.20A
FIG.20B

FIG.22

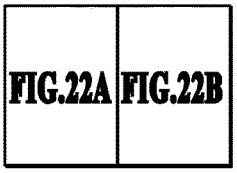

| GROUP | A | |
|---|---|---|
| RESISTANCE TO OZONE WATER | GOOD | |
| | NOT CORRODED OR DETERIORATED BY OZONE WATER | |
| | RESINS | INORGANIC MATERIALS |
| MAIN MATERIALS | ·FLUORORESIN (PTFE, PFA)<br>·FLUORORUBBER (FEPM, FKM) | ·TITANIUM<br>·TANTALUM<br>·IRIDIUM<br>·STAINLESS STEEL (SUS 316/316L)<br>·BOROSILICATE GLASS (PYREX)<br>·ALUMINA CERAMICS |
| T-UFB HEAD MEMBER | FLOW CHANNEL MEMBER<br>TUBES<br>TUBE JOINTS<br>SEAL MEMBER | FLOW CHANNEL MEMBER<br>TUBE JOINTS<br>ELEMENT SUBSTRATE (ANTI-CAVITATION FILM)<br>SUPPORT SUBSTRATE |

NOTES:
PTFE: POLYTETRAFLUOROETHYLENE
PFA: PERFLUOROALKOXY ALKANES
FEPM: TETRAFLUORO ETHYLENE-PERFLUORO VINYL ETHER
FKM: VINYLIDENE FLUORIDE
PPE: POLYPHENYLENE ETHER
PPS: POLYPHENYLENE SULFIDE
PS: POLYSTYRENE
NORYL: HOW MODIFIED PPE RESINS ARE TYPICALLY CALLED
SU-8: PHOTO-CURABLE NEGATIVE RESIST MADE MAINLY OF PGMEA (2 METHOXY 1 METHYLETHYL ACETATE)

FIG.22A

| B | C |
|---|---|
| USABLE UNDER CERTAIN CONDITIONS | UNUSABLE |
| SOME OF THEM MAY BE USED AFTER FORMING PASSIVATION FILM OR OXIDE FILM | RESIN COMES OFF FROM SURFACE AND MIXES INTO LIQUID AS IMPURITY. NOT SUITABLE FOR USE BECAUSE IT IS MINUTE PARTICLE PASSING THROUGH 0.2-µ FILTER. |
| INORGANIC MATERIALS | RESINS AND INORGANIC MATERIALS |
| ·SILICON<br>·STAINLESS STEEL (AUSTENITIC) | ·MODIFIED PPE (NORYL)<br>·PPS<br>·PS<br>·EPOXY RESIN (SU-8)<br>·EPOXY RESIN (THERMOSETTING)<br>·SILICONE RESIN<br>·BRASS<br>·ALUMINUM<br>·STAINLESS STEEL (MARTENSITIC) |
| FLOW CHANNEL MEMBER<br>HEIGHT ADJUSTMENT MEMBERS | |

FIG.22B

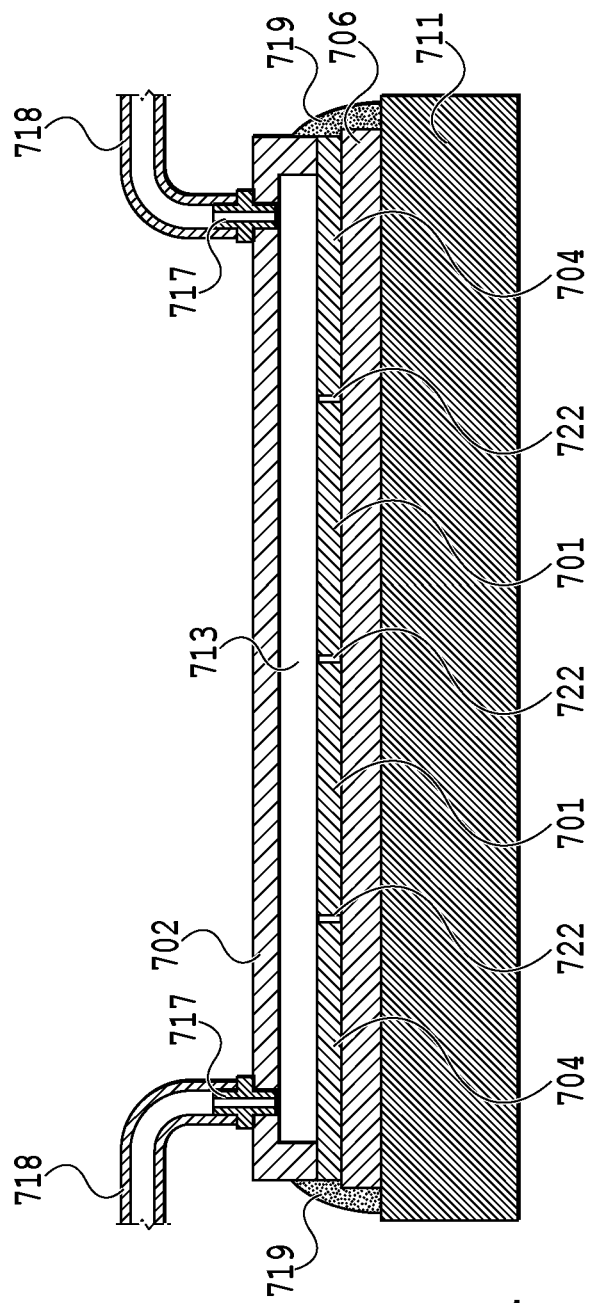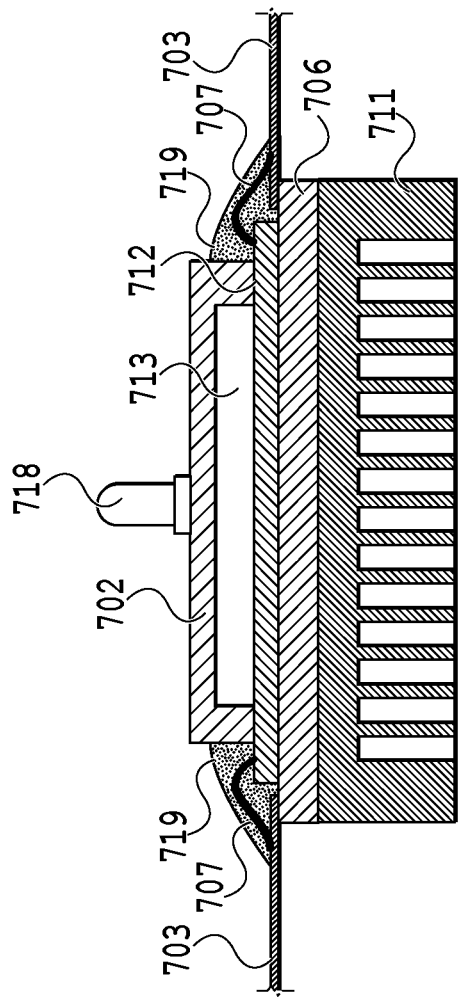
FIG.24A
FIG.24B

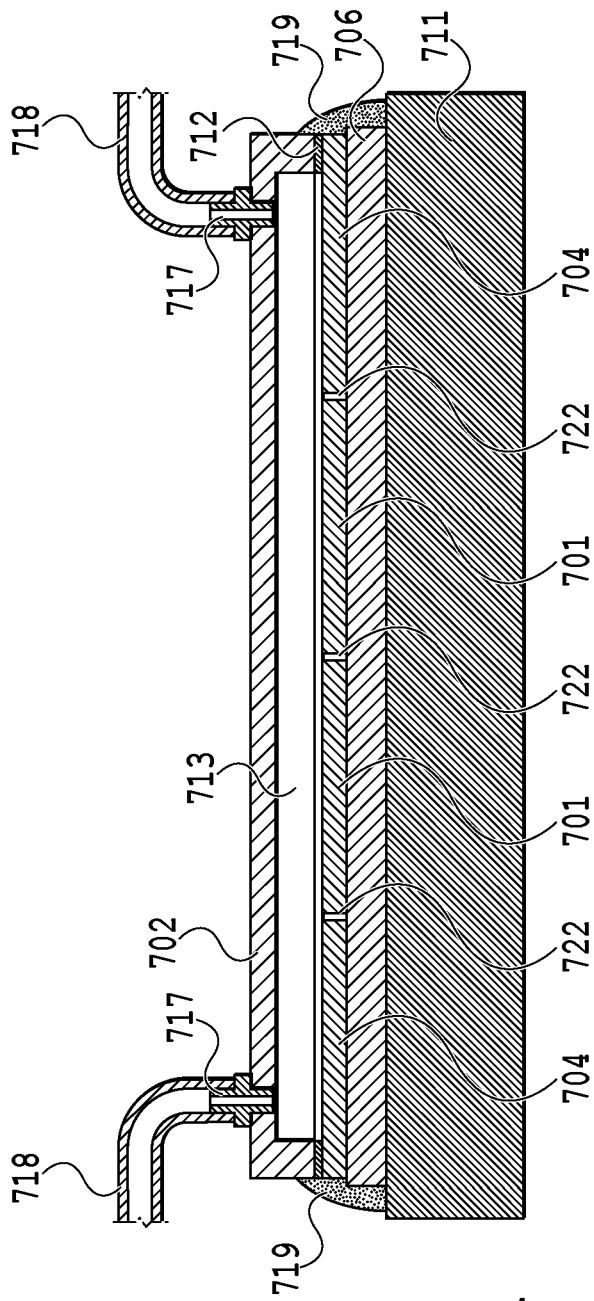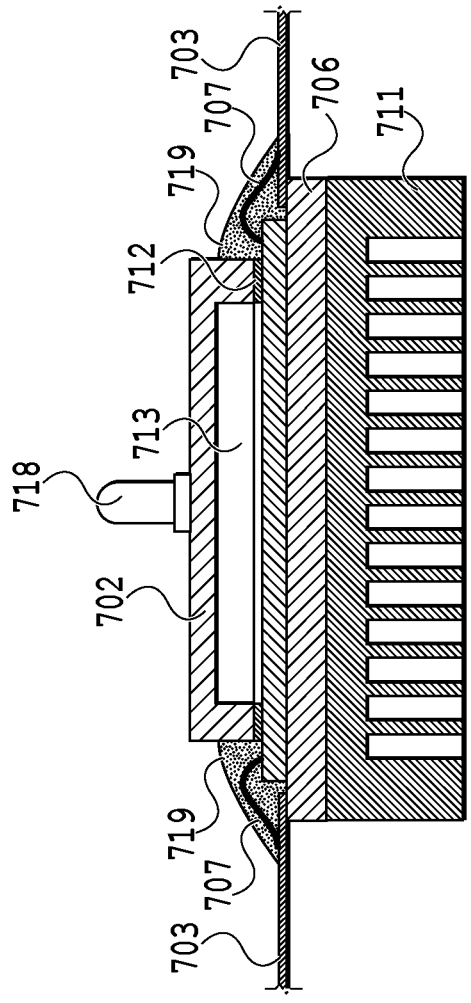
FIG.26A
FIG.26B

ULTRAFINE BUBBLE GENERATING APPARATUS AND ULTRAFINE BUBBLE GENERATING HEAD

BACKGROUND OF THE INVENTION

Field of the Invention

The present invention relates to an ultrafine bubble generating apparatus and an ultrafine bubble generating head for generating ultrafine bubbles with a diameter of less than 1.0 m.

Description of the Related Art

In recent years, there have been developed techniques to which the characteristics of fine bubbles, such as microbubbles with a micrometer-size diameter and nanobubbles with a nanometer-size diameter, are applied. Above all, ultrafine bubbles (UFBs) with a diameter of less than 1.0 m have been found useful in various fields. In particular, there are increasing demands for ozone UFB-contained water containing ozone UFBs because it is useful in applications such as surface modification, sterilization, and disinfection.

Japanese Patent Laid-Open No. 2019-042732 discloses a method and an apparatus for efficiently generating ozone UFBs with excellent stability by causing film boiling in a liquid in which an ozone gas is dissolved (hereinafter also referred to as "ozone water").

However, a UFB generating apparatus using ozone water may be at risk of corrosion and deterioration of a metal or an organic matter that forms a component such as a flow channel or a substrate that comes into contact with ozone water. A corroded or deteriorated material may come off a member and be mixed into the UFB-contained liquid as impurities, resulting in degrading the purity of and in turn the quality of the ozone UFB-contained liquid generated.

SUMMARY OF THE INVENTION

The present invention has been made to overcome the above problem, and has an object to provide a UFB generating apparatus capable of manufacturing an ozone UFB-contained liquid with high purity and quality.

In a first aspect of the present invention, there is provided an ultrafine bubble generating apparatus capable of generating ultrafine bubbles containing ozone by causing film boiling in ozone water, wherein a liquid contact portion that comes into contact with the ozone water is made of a material with corrosion resistance to ozone water.

In a second aspect of the present invention, there is provided an ultrafine bubble generating head comprising an element substrate on which a heating element is placed, the heating element generating heat upon application of voltage thereto and thereby causes film boiling in ozone water, and a flow channel member that forms a liquid flow channel which faces the element substrate and which contains the ozone water, wherein the element substrate is a silicon substrate whose surface to come into contact with the ozone water has been subjected to a process for enhancing corrosion resistance, and the flow channel member is made of stainless steel or borosilicate glass.

Further features of the present invention will become apparent from the following description of exemplary embodiments with reference to the attached drawings.

BRIEF DESCRIPTION OF THE DRAWINGS

FIGS. 20A and 20B are sectional views of the UFB generating head of the fourth embodiment;

FIG. 22 is a diagram showing the relationship of FIGS. 22A and 22B;

FIG. 22A is a diagram showing results of comparison between materials about their degrees of corrosion and deterioration;

FIG. 22B is a diagram showing results of comparison between materials about their degrees of corrosion and deterioration;

FIGS. 24A and 24B are sectional views of a UFB generating head of the fifth embodiment;

FIGS. 26A and 26B are sectional views of the UFB generating head of the sixth embodiment.

DESCRIPTION OF THE EMBODIMENTS

<<Outline of a UFB Generating Apparatus>>

An outline of a UFB generating apparatus that utilizes the film boiling phenomenon is described below.

Figure 1:
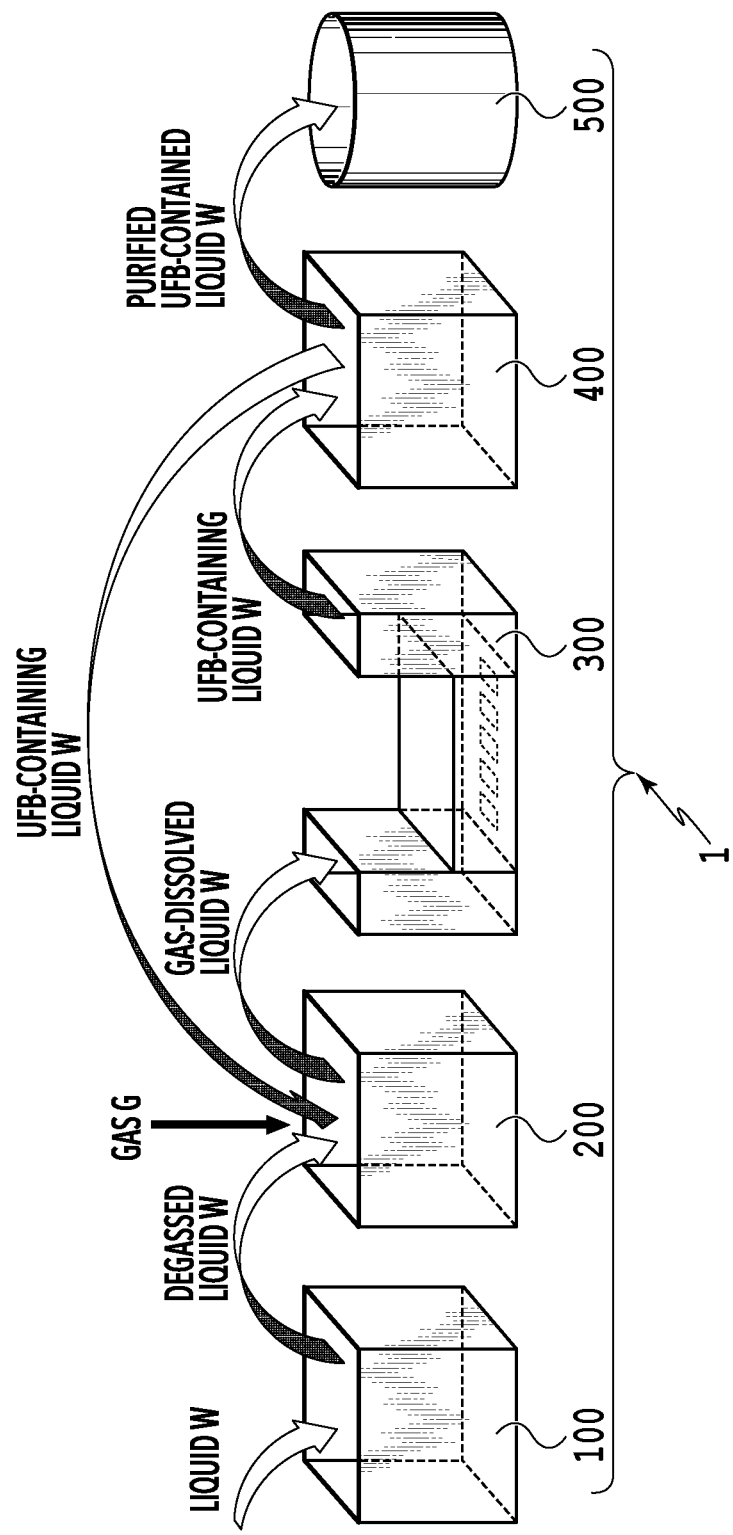
FIG. 1 is a diagram showing an example of a UFB generating apparatus.

FIG. 1 is a diagram illustrating an example of a UFB generating apparatus applicable to the present invention. A UFB generating apparatus 1 includes a pre-processing unit 100, dissolving unit 200, a T-UFB generating unit 300, a post-processing unit 400, and a collecting unit 500. Each unit performs unique processing on a liquid W such as tap water supplied to the pre-processing unit 100 in the above order, and the thus-processed liquid W is collected as a T-UFB-containing liquid by the collecting unit 500. Functions and configurations of the units are described below. Although details are described later, UFBs generated by utilizing the film boiling caused by rapid heating are referred to as thermal-ultrafine bubbles (T-UFBs) in this specification.

Figure 2:
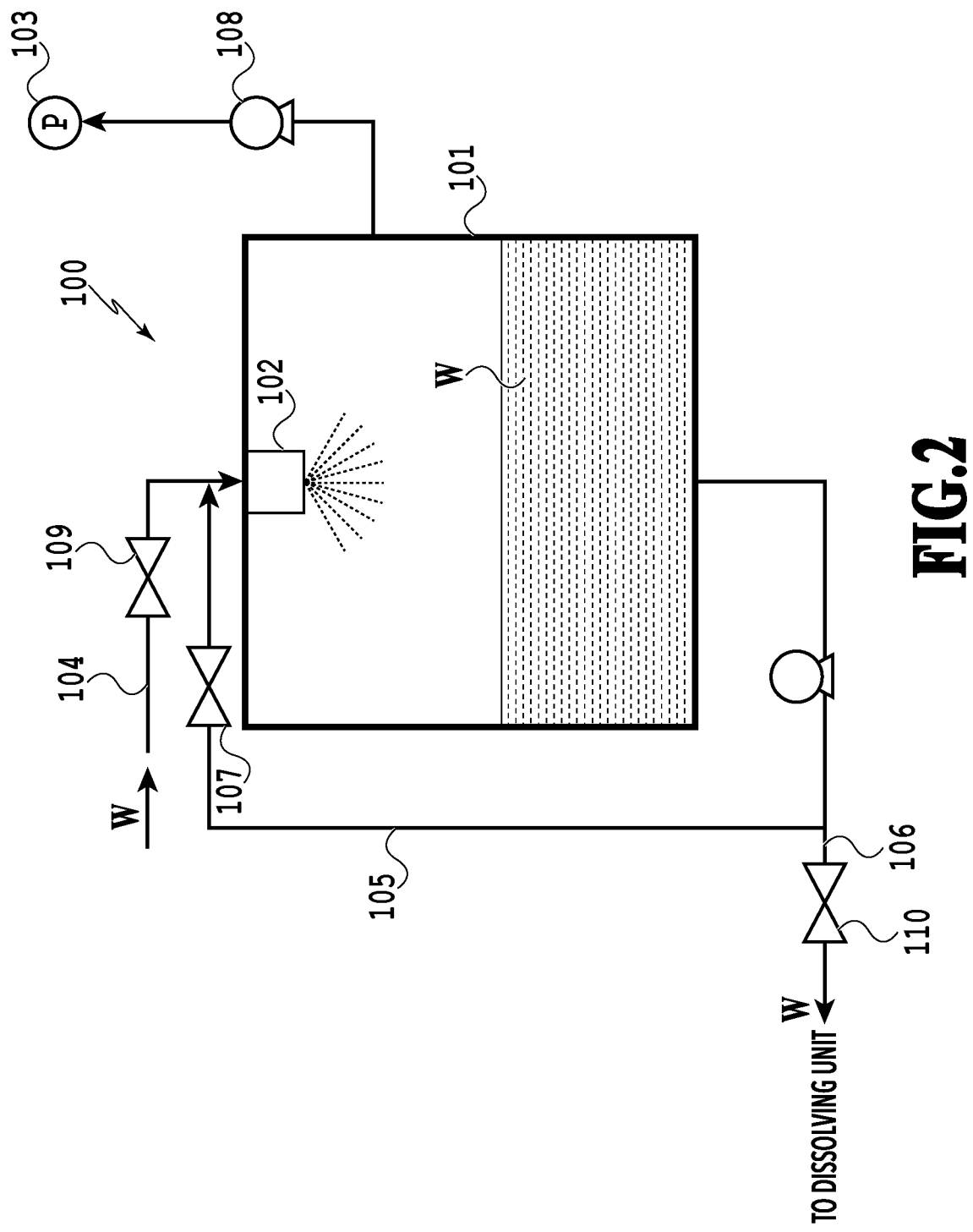
FIG. 2 is a diagram showing a schematic configuration of a pretreatment unit.

FIG. 2 is a schematic configuration diagram of the pre-processing unit 100. The pre-processing unit 100 performs a degassing treatment on the supplied liquid W. The pre-processing unit 100 mainly includes a degassing container 101, a shower head 102, a depressurizing pump 103, a liquid introduction passage 104, a liquid circulation passage 105, and a liquid discharge passage 106. For example, the liquid W such as tap water is supplied to the degassing container 101 from the liquid introduction passage 104 through a valve 109. In this process, the shower head 102 provided in the degassing container 101 sprays a mist of the liquid W in the degassing container 101. The shower head 102 is for prompting the gasification of the liquid W; however, a centrifugal and the like may be used instead as the mechanism for producing the gasification prompt effect.

When a certain amount of the liquid W is reserved in the degassing container 101 and then the depressurizing pump 103 is activated with all the valves closed, already-gasified gas components are discharged, and gasification and discharge of gas components dissolved in the liquid W are also prompted. In this process, the internal pressure of the degassing container 101 may be depressurized to around several hundreds to thousands of Pa (1.0 Torr to 10.0 Torr) while checking a manometer 108. The gases to be removed by the pre-processing unit 100 includes nitrogen, oxygen, argon, carbon dioxide, and so on, for example.

The above-described degassing processing can be repeatedly performed on the same liquid W by utilizing the liquid circulation passage 105. Specifically, the shower head 102 is operated with the valve 109 of the liquid introduction passage 104 and a valve 110 of the liquid discharge passage 106 closed and a valve 107 of the liquid circulation passage 105 opened. This allows the liquid W reserved in the degassing container 101 and degassed once to be resprayed in the degassing container 101 from the shower head 102. In addition, with the depressurizing pump 103 operated, the gasification processing by the shower head 102 and the degassing processing by the depressurizing pump 103 are repeatedly performed on the same liquid W. Every time the above processing utilizing the liquid circulation passage 105 is performed repeatedly, it is possible to decrease the gas components contained in the liquid W in stages. Once the liquid W degassed to a desired purity is obtained, the liquid W is transferred to the dissolving unit 200 through the liquid discharge passage 106 with the valve 110 opened.

FIG. 2 illustrates the degassing unit 100 that depressurizes the gas part to gasify the solute; however, the method of degassing the solution is not limited thereto. For example, a heating and boiling method for boiling the liquid W to gasify the solute may be employed, or a film degassing method for increasing the interface between the liquid and the gas using hollow fibers. A SEPAREL series (produced by DIC corporation) is commercially supplied as the degassing module using the hollow fibers. The SEPAREL series uses poly(4-methylpentene-1) (PMP) for the raw material of the hollow fibers and is used for removing air bubbles from ink and the like mainly supplied for a piezo head. In addition, two or more of an evacuating method, the heating and boiling method, and the film degassing method may be used together.

Figure 3A:
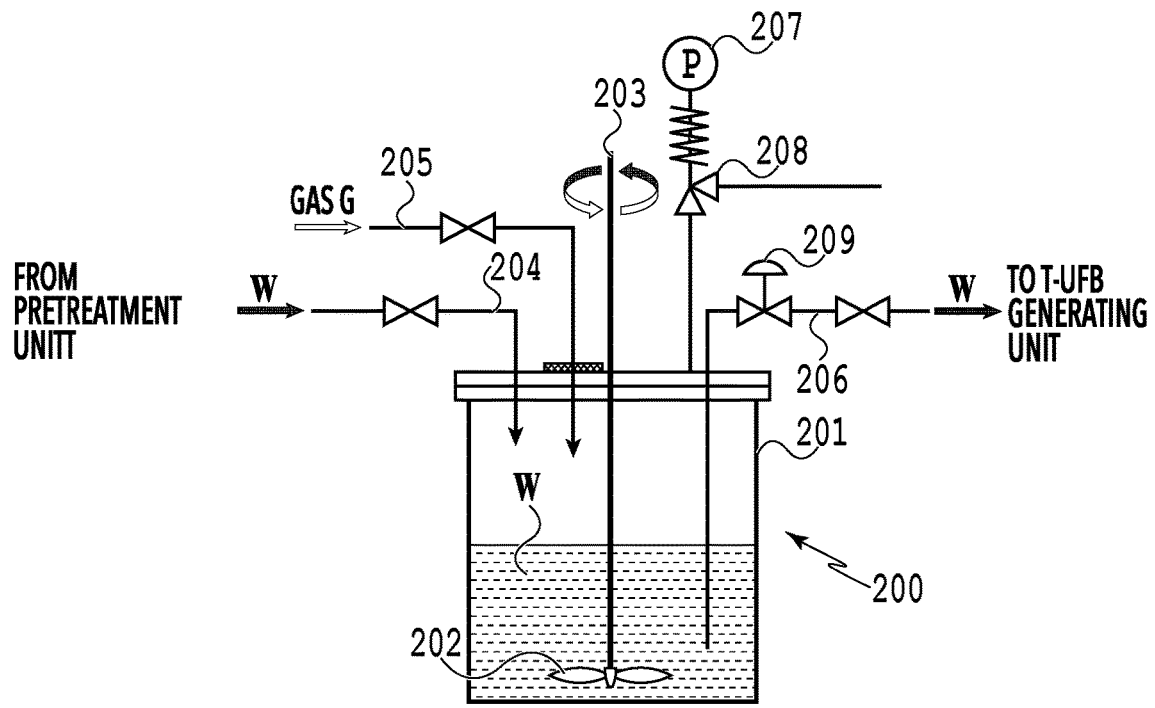
FIG. 3A is a diagram showing a schematic configuration of a dissolving unit.
Figure 3B:
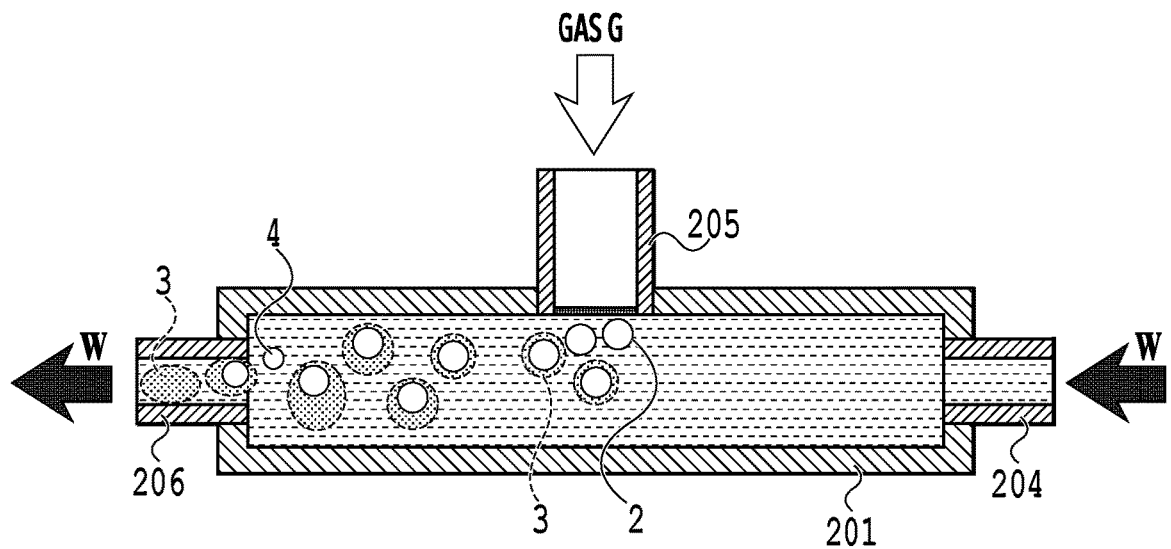
FIG. 3B is a diagram illustrating how a gas is dissolved in a liquid.

FIGS. 3A and 3B are a schematic configuration diagram of the dissolving unit 200 and a diagram for describing the dissolving states in the liquid. The dissolving unit 200 is a unit for dissolving a desired gas into the liquid W supplied from the pre-processing unit 100. The dissolving unit 200 mainly includes a dissolving container 201, a rotation shaft 203 provided with a rotation plate 202, a liquid introduction passage 204, a gas introduction passage 205, a liquid discharge passage 206, and a pressurizing pump 207.

The liquid W supplied from the pre-processing unit 100 is supplied and reserved into the dissolving container 201 through the liquid introduction passage 204. Meanwhile, a gas G is supplied to the dissolving container 201 through the gas introduction passage 205.

Once predetermined amounts of the liquid W and the gas G are reserved in the dissolving container 201, the pressurizing pump 207 is activated to increase the internal pressure of the dissolving container 201 to about 0.5 MPa. A safety valve 208 is arranged between the pressurizing pump 207 and the dissolving container 201. With the rotation plate 202 in the liquid rotated via the rotation shaft 203, the gas G supplied to the dissolving container 201 is transformed into air bubbles, and the contact area between the gas G and the liquid W is increased to prompt the dissolution into the liquid W. This operation is continued until the solubility of the gas G reaches almost the maximum saturation solubility. In this case, a unit for decreasing the temperature of the liquid may be provided to dissolve the gas as much as possible. When the gas is with low solubility, it is also possible to increase the internal pressure of the dissolving container 201 to 0.5 MPa or higher. In this case, the material and the like of the container need to be the optimum for safety sake.

Once the liquid W in which the components of the gas G are dissolved at a desired concentration is obtained, the liquid W is discharged through the liquid discharge passage 206 and supplied to the T-UFB generating unit 300. In this process, a back-pressure valve 209 adjusts the flow pressure of the liquid W to prevent excessive increase of the pressure during the supplying.

FIG. 3B is a diagram schematically illustrating the dissolving states of the gas G put in the dissolving container 201. An air bubble 2 containing the components of the gas G put in the liquid W is dissolved from a portion in contact with the liquid W. The air bubble 2 thus shrinks gradually, and a gas-dissolved liquid 3 then appears around the air bubble 2. Since the air bubble 2 is affected by the buoyancy, the air bubble 2 may be moved to a position away from the center of the gas-dissolved liquid 3 or be separated out from the gas-dissolved liquid 3 to become a residual air bubble 4. Specifically, in the liquid W to be supplied to the T-UFB generating unit 300 through the liquid discharge passage 206, there is a mix of the air bubbles 2 surrounded by the gas-dissolved liquids 3 and the air bubbles 2 and the gas-dissolved liquids 3 separated from each other.

The gas-dissolved liquid 3 in the drawings means "a region of the liquid W in which the dissolution concentration of the gas G mixed therein is relatively high." In the gas components actually dissolved in the liquid W, the concentration of the gas components in the gas-dissolved liquid 3 is the highest at a portion surrounding the air bubble 2. In a case where the gas-dissolved liquid 3 is separated from the air bubble 2 the concentration of the gas components of the gas-dissolved liquid 3 is the highest at the center of the region, and the concentration is continuously decreased as away from the center. That is, although the region of the gas-dissolved liquid 3 is surrounded by a broken line in FIG. 3 for the sake of explanation, such a clear boundary does not actually exist. In addition, in the present invention, a gas that cannot be dissolved completely may be accepted to exist in the form of an air bubble in the liquid.

Figure 4:
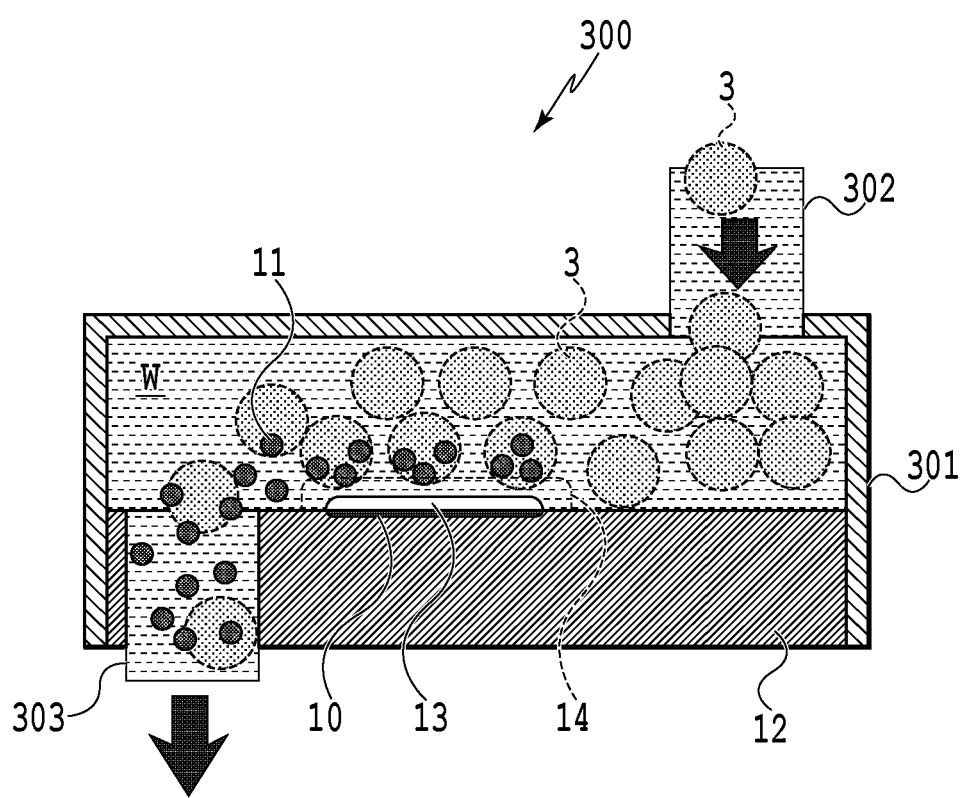
FIG. 4 is a diagram showing a schematic configuration of a T-UFB generating unit.

FIG. 4 is a schematic configuration diagram of the T-UFB generating unit 300. The T-UFB generating unit 300 mainly includes a chamber 301, a liquid introduction passage 302, and a liquid discharge passage 303. The flow from the liquid introduction passage 302 to the liquid discharge passage 303 through the chamber 301 is formed by a not-illustrated flow pump. Various pumps including a diaphragm pump, a gear pump, and a screw pump may be employed as the flow pump. In in the liquid W introduced from the liquid introduction passage 302, the gas-dissolved liquid 3 of the gas G put by the dissolving unit 200 is mixed.

An element substrate 12 provided with a heating element 10 is arranged on a bottom section of the chamber 301. With a predetermined voltage pulse applied to the heating element 10, a bubble 13 generated by the film boiling (hereinafter, also referred to as a film boiling bubble 13) is generated in a region in contact with the heating element 10. Then, an ultrafine bubble (UFB) 11 containing the gas G is generated caused by expansion and shrinkage of the film boiling bubble 13. As a result, a UFB-containing liquid W containing many UFBs 11 is discharged from the liquid discharge passage 303.

Figure 5A:
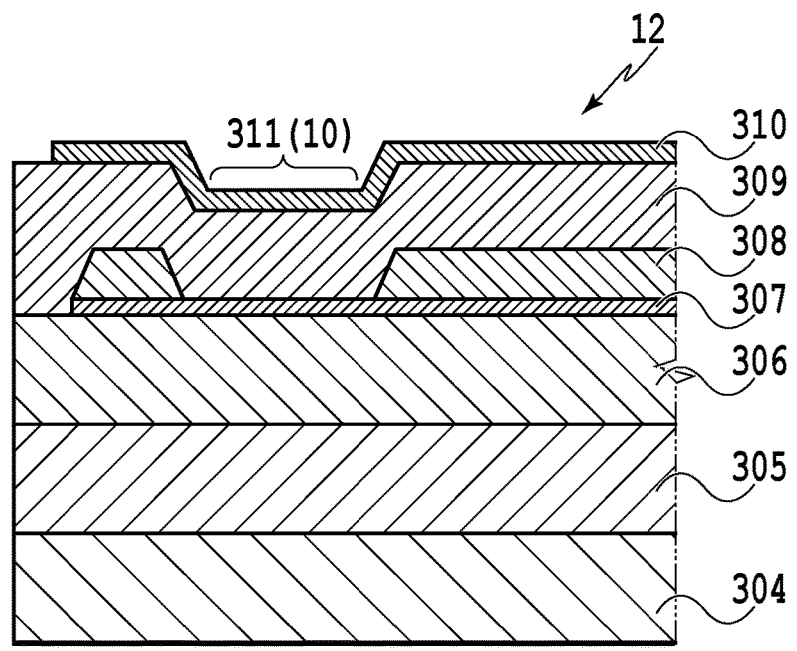
FIGS. 5A and 5B are diagrams illustrating a heating element in detail.
Figure 5B:
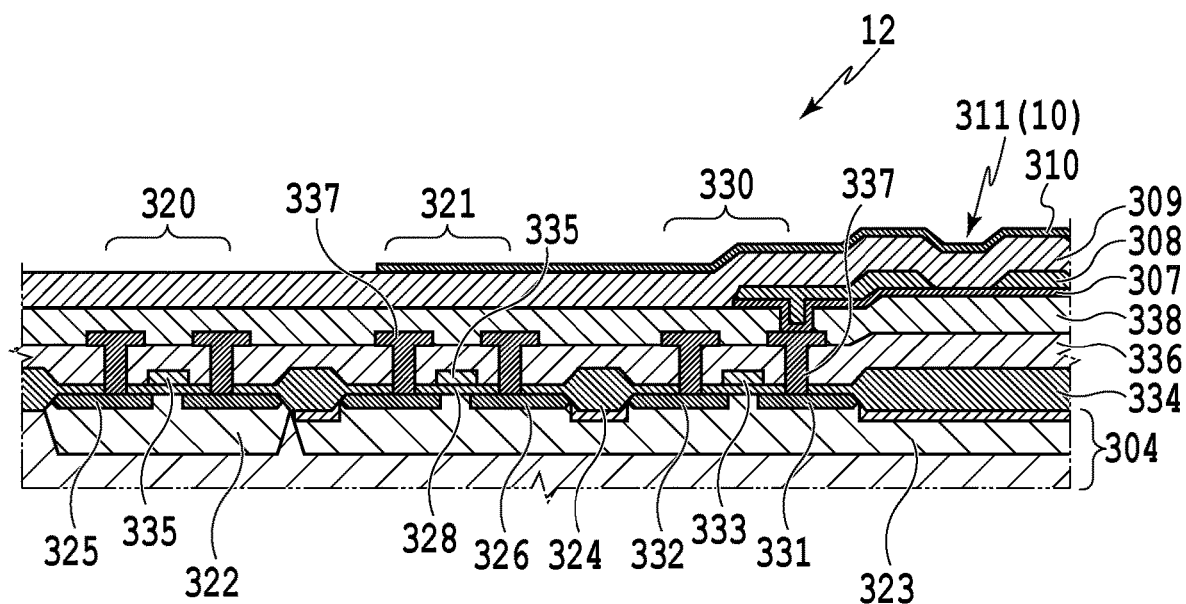

FIGS. 5A and 5B are diagrams for illustrating a detailed configuration of the heating element 10. FIG. 5A illustrates a closeup view of the heating element 10, and FIG. 5B illustrates a cross-sectional view of a wider region of the element substrate 12 including the heating element 10.

As illustrated in FIG. 5A, in the element substrate 12, a thermal oxide film 305 as a heat-accumulating layer and an interlaminar film 306 also served as a heat-accumulating layer are laminated on a surface of a silicon substrate 304. An $SiO_2$ film or an SiN film may be used as the interlaminar film 306. A resistive layer 307 is formed on a surface of the interlaminar film 306, and a wiring 308 is partially formed on a surface of the resistive layer 307. An Al-alloy wiring of Al, Al—Si, Al—Cu, or the like may be used as the wiring 308. A protective layer 309 made of an $SiO_2$ film or an $Si_3N_4$ film is formed on surfaces of the wiring 308, the resistive layer 307, and the interlaminar film 306.

A cavitation-resistant film 310 for protecting the protective layer 309 from chemical and physical impacts due to the heat evolved by the resistive layer 307 is formed on a portion and around the portion on the surface of the protective layer 309, the portion corresponding to a heat-acting portion 311 that eventually becomes the heating element 10. A region on the surface of the resistive layer 307 in which the wiring 308 is not formed is the heat-acting portion 311 in which the resistive layer 307 evolves heat. The heating portion of the resistive layer 307 on which the wiring 308 is not formed functions as the heating element (heater) 10. As described above, the layers in the element substrate 12 are sequentially formed on the surface of the silicon substrate 304 by a semiconductor production technique, and the heat-acting portion 311 is thus provided on the silicon substrate 304.

The configuration illustrated in the drawings is an example, and various other configurations are applicable. For example, a configuration in which the laminating order of the resistive layer 307 and the wiring 308 is opposite, and a configuration in which an electrode is connected to a lower surface of the resistive layer 307 (so-called a plug electrode configuration) are applicable. In other words, as described later, any configuration may be applied as long as the configuration allows the heat-acting portion 311 to heat the liquid for generating the film boiling in the liquid.

FIG. 5B is an example of a cross-sectional view of a region including a circuit connected to the wiring 308 in the element substrate 12. An N-type well region 322 and a P-type well region 323 are partially provided in a top layer of the silicon substrate 304, which is a P-type conductor. A P-MOS 320 is formed in the N-type well region 322 and an N-MOS 321 is formed in the P-type well region 323 by introduction and diffusion of impurities by the ion implantation and the like in the general MOS process.

The P-MOS 320 includes a source region 325 and a drain region 326 formed by partial introduction of N-type or P-type impurities in a top layer of the N-type well region 322, a gate wiring 335, and so on. The gate wiring 335 is deposited on a part of a top surface of the N-type well region 322 excluding the source region 325 and the drain region 326, with a gate insulation film 328 of several hundreds of Å in thickness interposed between the gate wiring 335 and the top surface of the N-type well region 322.

The N-MOS 321 includes the source region 325 and the drain region 326 formed by partial introduction of N-type or P-type impurities in a top layer of the P-type well region 323, the gate wiring 335, and so on. The gate wiring 335 is deposited on a part of a top surface of the P-type well region 323 excluding the source region 325 and the drain region 326, with the gate insulation film 328 of several hundreds of Å in thickness interposed between the gate wiring 335 and the top surface of the P-type well region 323. The gate wiring 335 is made of polysilicon of 3000 Å to 5000 Å in thickness deposited by the CVD method. A C-MOS logic is constructed with the P-MOS 320 and the N-MOS 321.

In the P-type well region 323, an N-MOS transistor 330 for driving an electrothermal conversion element (heating resistance element) is formed on a portion different from the portion including the N-MOS 321. The N-MOS transistor 330 includes a source region 332 and a drain region 331 partially provided in the top layer of the P-type well region 323 by the steps of introduction and diffusion of impurities, a gate wiring 333, and so on. The gate wiring 333 is deposited on a part of the top surface of the P-type well region 323 excluding the source region 332 and the drain region 331, with the gate insulation film 328 interposed between the gate wiring 333 and the top surface of the P-type well region 323.

In this example, the N-MOS transistor 330 is used as the transistor for driving the electrothermal conversion element. However, the transistor for driving is not limited to the N-MOS transistor 330, and any transistor may be used as long as the transistor has a capability of driving multiple electrothermal conversion elements individually and can implement the above-described fine configuration. Although the electrothermal conversion element and the transistor for driving the electrothermal conversion element are formed on the same substrate in this example, those may be formed on different substrates separately.

An oxide film separation region 324 is formed by field oxidation of 5000 Å to 10000 Å in thickness between the elements, such as between the P-MOS 320 and the N-MOS 321 and between the N-MOS 321 and the N-MOS transistor 330. The oxide film separation region 324 separates the elements. A portion of the oxide film separation region 324 corresponding to the heat-acting portion 311 functions as a heat-accumulating layer 334, which is the first layer on the silicon substrate 304.

An interlayer insulation film 336 including a PSG film, a BPSG film, or the like of about 7000 Å in thickness is formed by the CVD method on each surface of the elements such as the P-MOS 320, the N-MOS 321, and the N-MOS transistor 330. After the interlayer insulation film 336 is made flat by heat treatment, an Al electrode 337 as a first wiring layer is formed in a contact hole penetrating through the interlayer insulation film 336 and the gate insulation film 328. On surfaces of the interlayer insulation film 336 and the Al electrode 337, an interlayer insulation film 338 including an $SiO_2$ film of 10000 Å to 15000 Å in thickness is formed by a plasma CVD method. On the surface of the interlayer insulation film 338, a resistive layer 307 including a TaSiN film of about 500 Å in thickness is formed by a co-sputter method on portions corresponding to the heat-acting portion 311 and the N-MOS transistor 330. The resistive layer 307 is electrically connected with the Al electrode 337 near the drain region 331 via a through-hole formed in the interlayer insulation film 338. On the surface of the resistive layer 307, the wiring 308 of Al as a second wiring layer for a wiring to each electrothermal conversion element is formed. The protective layer 309 on the surfaces of the wiring 308, the resistive layer 307, and the interlayer insulation film 338 includes an SiN film of 3000 Å in thickness formed by the plasma CVD method. The cavitation-resistant film 310 deposited on the surface of the protective layer 309 includes a thin film of about 2000 Å in thickness, which is at least one metal selected from the group consisting of Ta, Fe, Ni, Cr, Ge, Ru, Zr, Ir, and the like. Various materials other than the above-described TaSiN such as $TaN_{0.8}$, CrSiN, TaAl, WSiN, and the like can be applied as long as the material can generate the film boiling in the liquid.

Figure 6A:
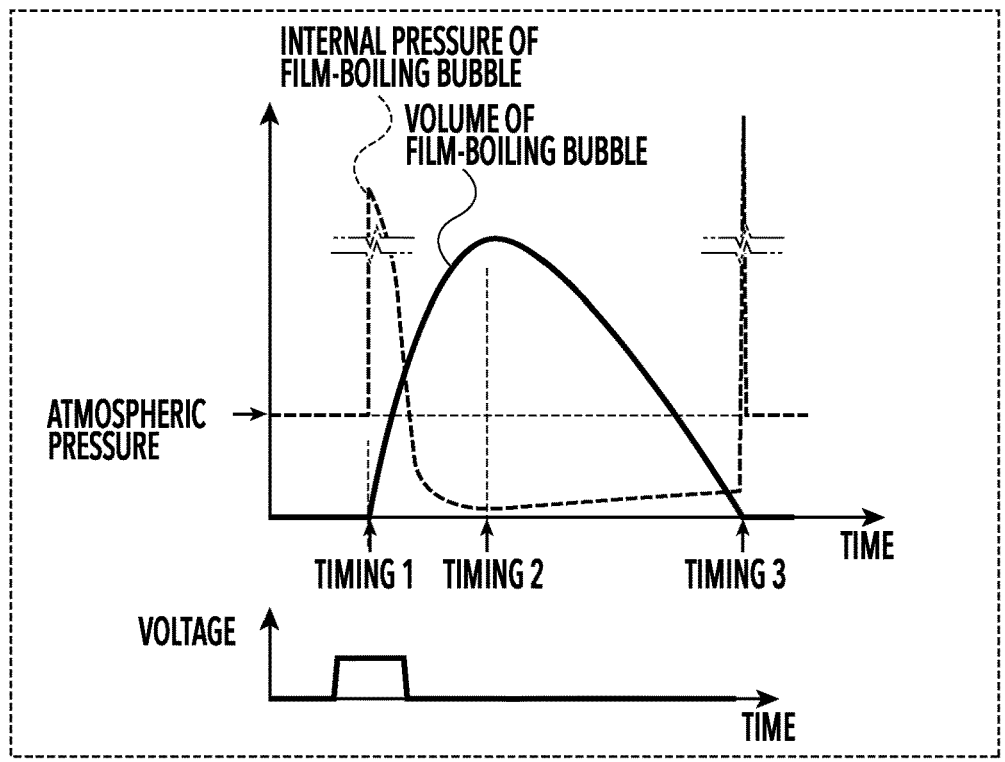
FIGS. 6A and 6B are diagrams illustrating how film boiling is caused by the heating elements.
Figure 6B:
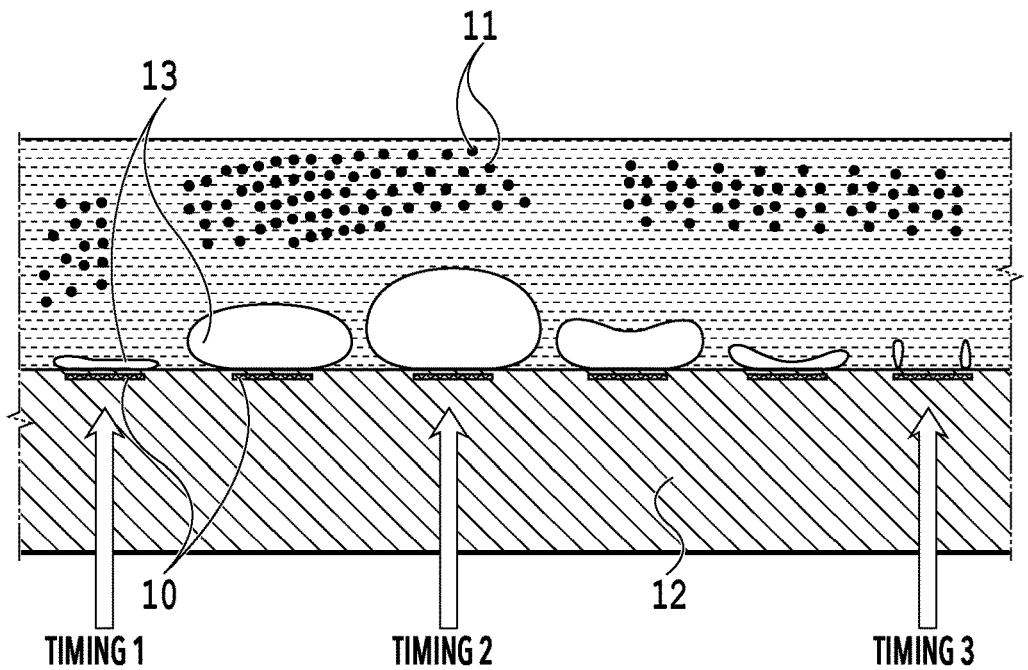

FIGS. 6A and 6B are diagrams illustrating the states of the film boiling when a predetermined voltage pulse is applied to the heating element 10. In this case, the case of generating the film boiling under atmospheric pressure is described. In FIG. 6A, the horizontal axis represents time. The vertical axis in the lower graph represents a voltage applied to the heating element 10, and the vertical axis in the upper graph represents the volume and the internal pressure of the film boiling bubble 13 generated by the film boiling. On the other hand, FIG. 6B illustrates the states of the film boiling bubble 13 in association with timings 1 to 3 shown in FIG. 6A. Each of the states is described below in chronological order. The UFBs 11 generated by the film boiling as described later are mainly generated near a surface of the film boiling bubble 13. The states illustrated in FIG. 6B are the states where the UFBs 11 generated by the generating unit 300 are resupplied to the dissolving unit 200 through the circulation route, and the liquid containing the UFBs 11 is resupplied to the liquid passage of the generating unit 300, as illustrated in FIG. 1.

Before a voltage is applied to the heating element 10, the atmospheric pressure is substantially maintained in the chamber 301. Once a voltage is applied to the heating element 10, the film boiling is generated in the liquid in contact with the heating element 10, and a thus-generated air bubble (hereinafter, referred to as the film boiling bubble 13) is expanded by a high pressure acting from inside (timing 1).

A bubbling pressure in this process is expected to be around 8 to 10 MPa, which is a value close to a saturation vapor pressure of water.

The time for applying a voltage (pulse width) is around 0.5 μsec to 10.0 μsec, and the film boiling bubble 13 is expanded by the inertia of the pressure obtained in timing 1 even after the voltage application. However, a negative pressure generated with the expansion is gradually increased inside the film boiling bubble 13, and the negative pressure acts in a direction to shrink the film boiling bubble 13. After a while, the volume of the film boiling bubble 13 becomes the maximum in timing 2 when the inertial force and the negative pressure are balanced, and thereafter the film boiling bubble 13 shrinks rapidly by the negative pressure.

In the disappearance of the film boiling bubble 13, the film boiling bubble 13 disappears not in the entire surface of the heating element 10 but in one or more extremely small regions. For this reason, on the heating element 10, further greater force than that in the bubbling in timing 1 is generated in the extremely small region in which the film boiling bubble 13 disappears (timing 3).

The generation, expansion, shrinkage, and disappearance of the film boiling bubble 13 as described above are repeated every time a voltage pulse is applied to the heating element 10, and new UFBs 11 are generated each time.

The states of generation of the UFBs 11 in each process of the generation, expansion, shrinkage, and disappearance of the film boiling bubble 13 are further described in detail with reference to FIGS. 7A to 10B.

Figure 7A:
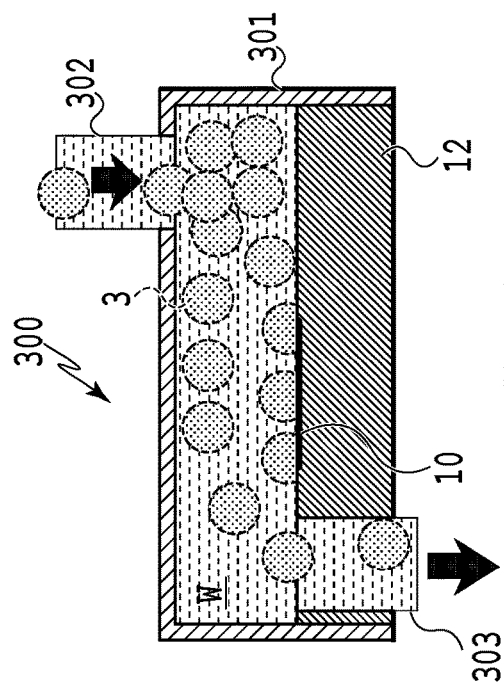
FIGS. 7A to 7D are diagrams showing how UFBs are generated by expansion of a film-boiling bubble.

FIGS. 7A to 7D are diagrams schematically illustrating the states of generation of the UFBs 11 caused by the generation and the expansion of the film boiling bubble 13. FIG. 7A illustrates the state before the application of a voltage pulse to the heating element 10. The liquid W in which the gas-dissolved liquids 3 are mixed flows inside the chamber 301.

Figure 7B:
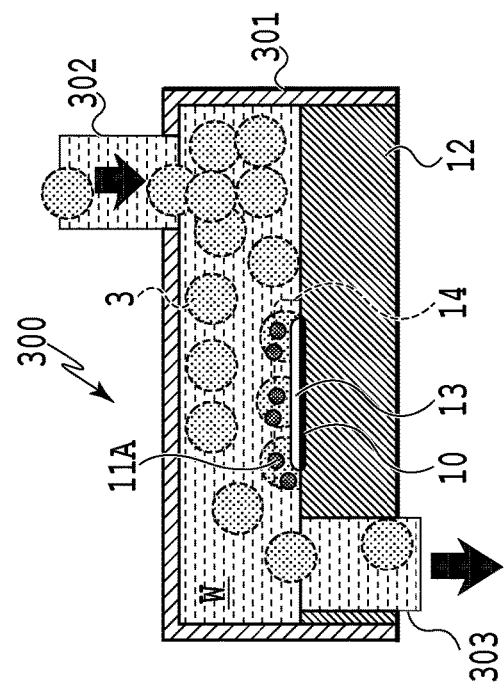

FIG. 7B illustrates the state where a voltage is applied to the heating element 10, and the film boiling bubble 13 is evenly generated in almost all over the region of the heating element 10 in contact with the liquid W. When a voltage is applied, the surface temperature of the heating element 10 rapidly increases at a speed of 10° C./μsec. The film boiling occurs at a time point when the temperature reaches almost 300° C., and the film boiling bubble 13 is thus generated.

Thereafter, the surface temperature of the heating element 10 keeps increasing to around 600 to 800° C. during the pulse application, and the liquid around the film boiling bubble 13 is rapidly heated as well. In FIG. 7B, a region of the liquid that is around the film boiling bubble 13 and to be rapidly (within 100 μs or less) heated is indicated as a not-yet-bubbling high temperature region 14. The gas-dissolved liquid 3 within the not-yet-bubbling high temperature region 14 exceeds the thermal dissolution limit and is vaporized to become the UFB almost simultaneously. The thus-vaporized air bubbles have diameters of around 10 nm to 100 nm and large gas-liquid interface energy. Further, a liquid intervenes between bubbles. Thus, the air bubbles float independently in the liquid W without disappearing in a short time. The air bubbles generated by the thermal action from the generation to the expansion of the film boiling bubble 13 are called first UFBs 11A.

Figure 7C:
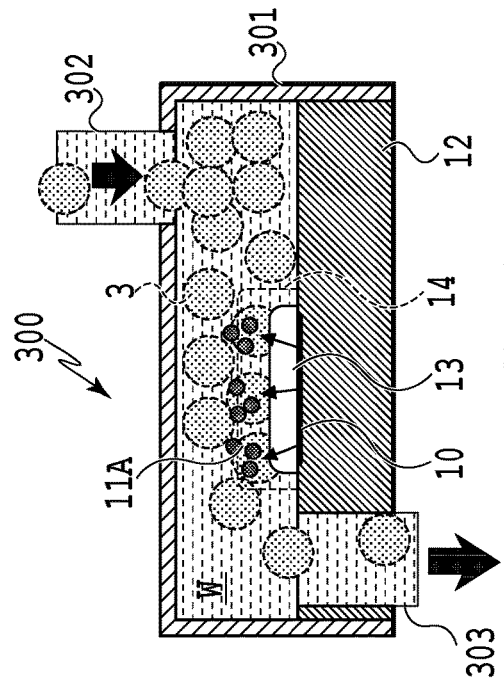

FIG. 7C illustrates the state where the film boiling bubble 13 is expanded. Even after the voltage pulse application to the heating element 10, the film boiling bubble 13 continues expansion by the inertia of the force obtained from the generation thereof, and the not-yet-bubbling high temperature region 14 is also moved and spread by the inertia.

Specifically, in the process of the expansion of the film boiling bubble 13, the gas-dissolved liquid 3 within the not-yet-bubbling high temperature region 14 is vaporized as a new air bubble and becomes the first UFB 11A.

Figure 7D:
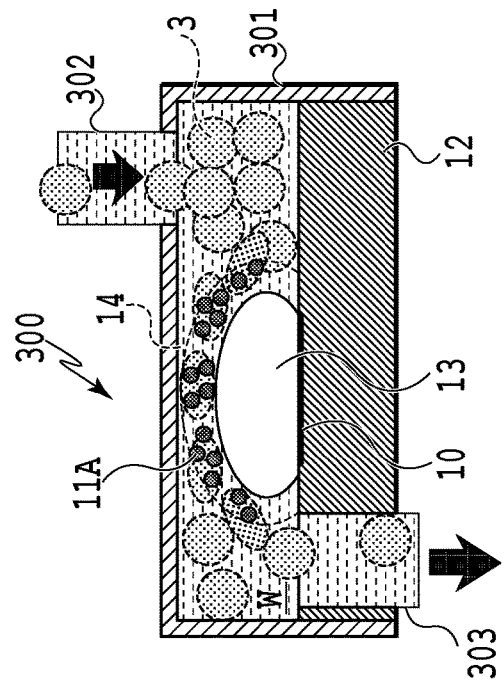

FIG. 7D illustrates the state where the film boiling bubble 13 has the maximum volume. As the film boiling bubble 13 is expanded by the inertia, the negative pressure inside the film boiling bubble 13 is gradually increased along with the expansion, and the negative pressure acts to shrink the film boiling bubble 13. At a time point when the negative pressure and the inertial force are balanced, the volume of the film boiling bubble 13 becomes the maximum, and then the shrinkage is started.

Figure 8A:
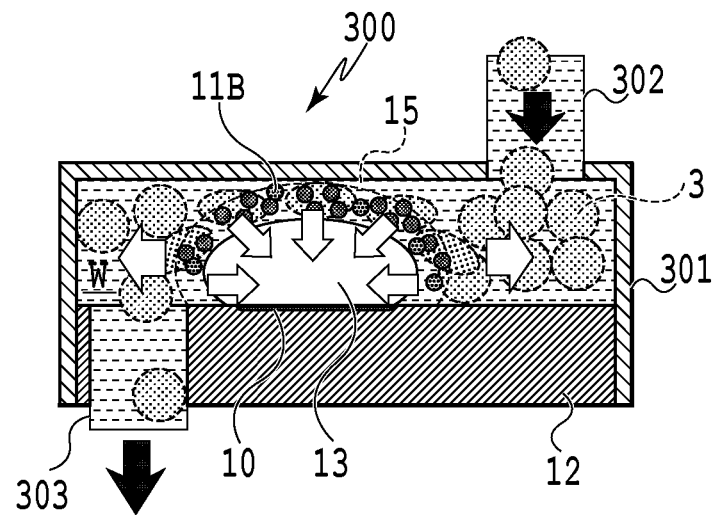
FIGS. 8A to 8C are diagrams showing how UFBs are generated by contraction of a film-boiling bubble.
Figure 8B:
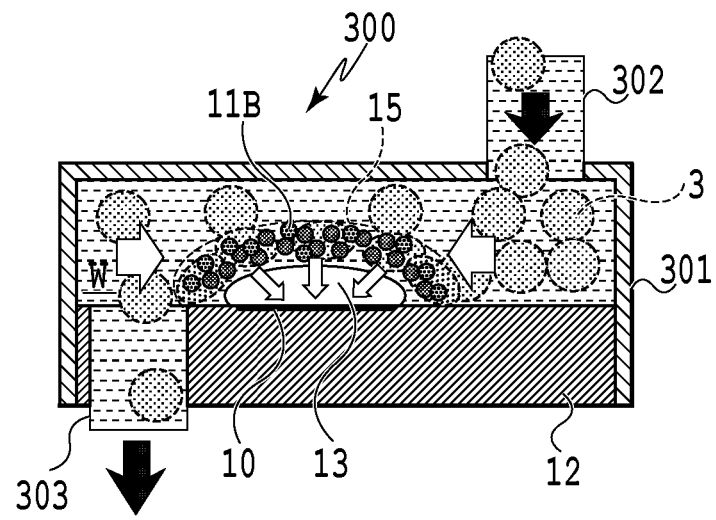
Figure 8C:
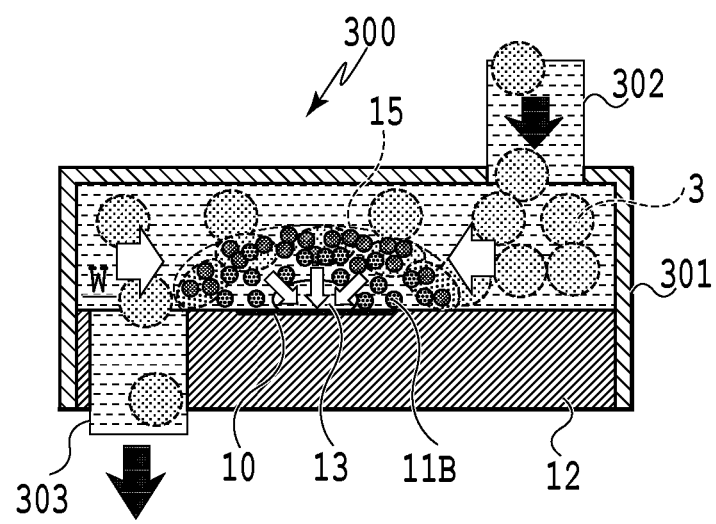
Figure 9A:
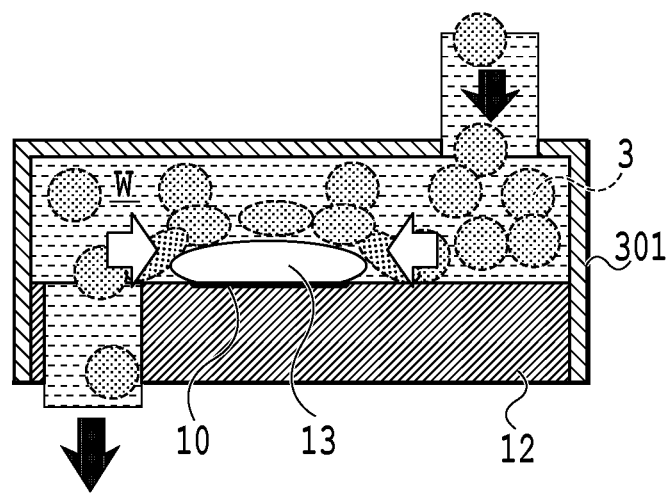
FIGS. 9A to 9C are diagrams showing how UFBs are generated by re-heating of liquid.
Figure 9B:
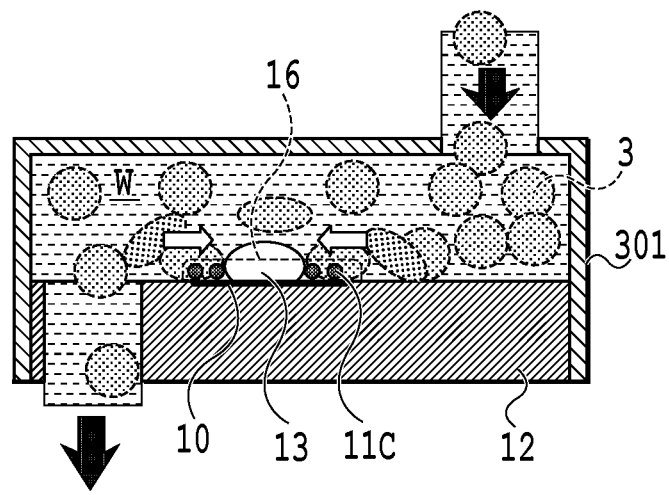
Figure 9C:
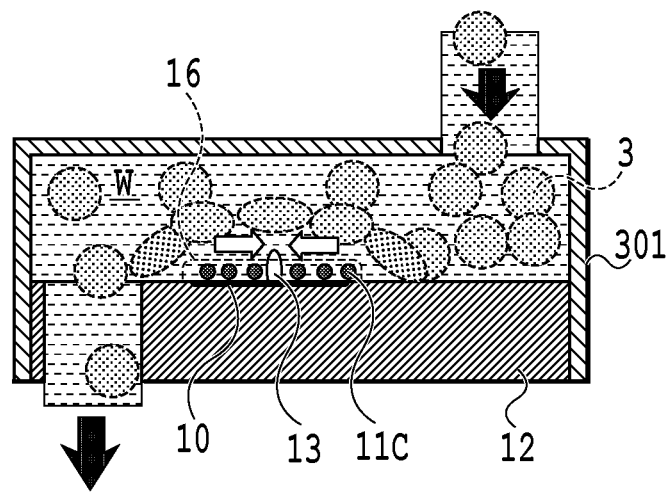

In the shrinking stage of the film boiling bubble 13, there are UFBs generated by the processes illustrated in FIGS. 8A to 8C (second UFBs 11B) and UFBs generated by the processes illustrated in FIGS. 9A to 9C (third UFBs 11C). It is considered that these two processes are made simultaneously.

FIGS. 8A to 8C are diagrams illustrating the states of generation of the UFBs 11 caused by the shrinkage of the film boiling bubble 13. FIG. 8A illustrates the state where the film boiling bubble 13 starts shrinking. Although the film boiling bubble 13 starts shrinking, the surrounding liquid W still has the inertial force in the expansion direction. Because of this, the inertial force acting in the direction of going away from the heating element 10 and the force going toward the heating element 10 caused by the shrinkage of the film boiling bubble 13 act in a surrounding region extremely close to the film boiling bubble 13, and the region is depressurized. The region is indicated in the drawings as a not-yet-bubbling negative pressure region 15.

The gas-dissolved liquid 3 within the not-yet-bubbling negative pressure region 15 exceeds the pressure dissolution limit and is vaporized to become an air bubble. The thus-vaporized air bubbles have diameters of about 100 nm and thereafter float independently in the liquid W without disappearing in a short time. In this disclosure, the air bubbles vaporized by the pressure action during the shrinkage of the film boiling bubble 13 are called the second UFBs 11B.

FIG. 8B illustrates a process of the shrinkage of the film boiling bubble 13. The shrinking speed of the film boiling bubble 13 is accelerated by the negative pressure, and the not-yet-bubbling negative pressure region 15 is also moved along with the shrinkage of the film boiling bubble 13. Specifically, in the process of the shrinkage of the film boiling bubble 13, the gas-dissolved liquids 3 within a part over the not-yet-bubbling negative pressure region 15 are precipitated one after another and become the second UFBs 11B.

FIG. 8C illustrates the state immediately before the disappearance of the film boiling bubble 13. Although the moving speed of the surrounding liquid W is also increased by the accelerated shrinkage of the film boiling bubble 13, a pressure loss occurs due to a flow passage resistance in the chamber 301. As a result, the region occupied by the not-yet-bubbling negative pressure region 15 is further increased, and a number of the second UFBs 11B are generated.

FIGS. 9A to 9C are diagrams illustrating the states of generation of the UFBs by reheating of the liquid W during the shrinkage of the film boiling bubble 13. FIG. 9A illustrates the state where the surface of the heating element 10 is covered with the shrinking film boiling bubble 13.

FIG. 9B illustrates the state where the shrinkage of the film boiling bubble 13 has progressed, and a part of the surface of the heating element 10 comes in contact with the liquid W. In this state, there is heat left on the surface of the heating element 10, but the heat is not high enough to cause the film boiling even if the liquid W comes in contact with the surface. A region of the liquid to be heated by coming in contact with the surface of the heating element 10 is indicated in the drawings as a not-yet-bubbling reheated region 16. Although the film boiling is not made, the gas-dissolved liquid 3 within the not-yet-bubbling reheated region 16 exceeds the thermal dissolution limit and is vaporized. In this disclosure, the air bubbles generated by the reheating of the liquid W during the shrinkage of the film boiling bubble 13 are called the third UFBs 11C.

FIG. 9C illustrates the state where the shrinkage of the film boiling bubble 13 has further progressed. The smaller the film boiling bubble 13, the greater the region of the heating element 10 in contact with the liquid W, and the third UFBs 11C are generated until the film boiling bubble 13 disappears.

Figure 10A:
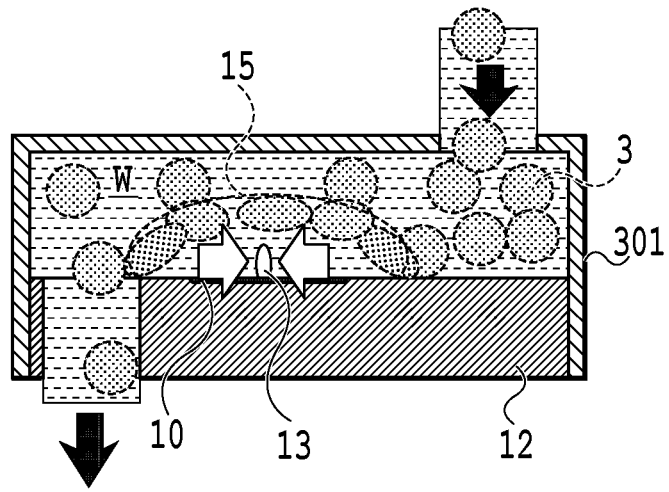
FIGS. 10A and 10B are diagrams showing how UFBs are generated by shock wave caused by the collapse of a bubble generated by film boiling.
Figure 10B:
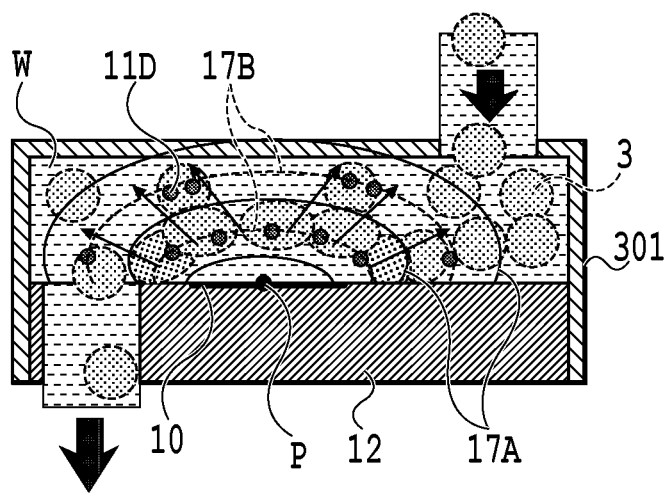

FIGS. 10A and 10B are diagrams illustrating the states of generation of the UFBs caused by an impact from the disappearance of the film boiling bubble 13 generated by the film boiling (that is, a type of cavitation). FIG. 10A illustrates the state immediately before the disappearance of the film boiling bubble 13. In this state, the film boiling bubble 13 shrinks rapidly by the internal negative pressure, and the not-yet-bubbling negative pressure region 15 surrounds the film boiling bubble 13.

FIG. 10B illustrates the state immediately after the film boiling bubble 13 disappears at a point P. When the film boiling bubble 13 disappears, acoustic waves ripple concentrically from the point P as a starting point due to the impact of the disappearance. The acoustic wave is a collective term of an elastic wave that is propagated through anything regardless of gas, liquid, and solid. Compression waves of the liquid W, which are a high pressure surface 17A and a low pressure surface 17B of the liquid W, are propagated alternately.

In this case, the gas-dissolved liquid 3 within the not-yet-bubbling negative pressure region 15 is resonated by the shock waves made by the disappearance of the film boiling bubble 13, and the gas-dissolved liquid 3 exceeds the pressure dissolution limit and the phase transition is made in timing when the low pressure surface 17B passes therethrough. Specifically, a number of air bubbles are vaporized in the not-yet-bubbling negative pressure region 15 simultaneously with the disappearance of the film boiling bubble 13. In this disclosure, the air bubbles generated by the shock waves made by the disappearance of the film boiling bubble 13 are called fourth UFBs 11D.

The fourth UFBs 11D generated by the shock waves made by the disappearance of the film boiling bubble 13 suddenly appear in an extremely short time (1 µS or less) in an extremely narrow thin film-shaped region. The diameter is sufficiently smaller than that of the first to third UFBs, and the gas-liquid interface energy is higher than that of the first to third UFBs. For this reason, it is considered that the fourth UFBs 11D have different characteristics from the first to third UFBs 11A to 11C and generate different effects.

Additionally, the fourth UFBs 11D are evenly generated in many parts of the region of the concentric sphere in which the shock waves are propagated, and the fourth UFBs 11D evenly exist in the chamber 301 from the generation thereof. Although many first to third UFBs already exist in the timing of the generation of the fourth UFBs 11D, the presence of the first to third UFBs does not affect the generation of the fourth UFBs 11D greatly. It is also considered that the first to third UFBs do not disappear due to the generation of the fourth UFBs 11D.

Figure 11A:
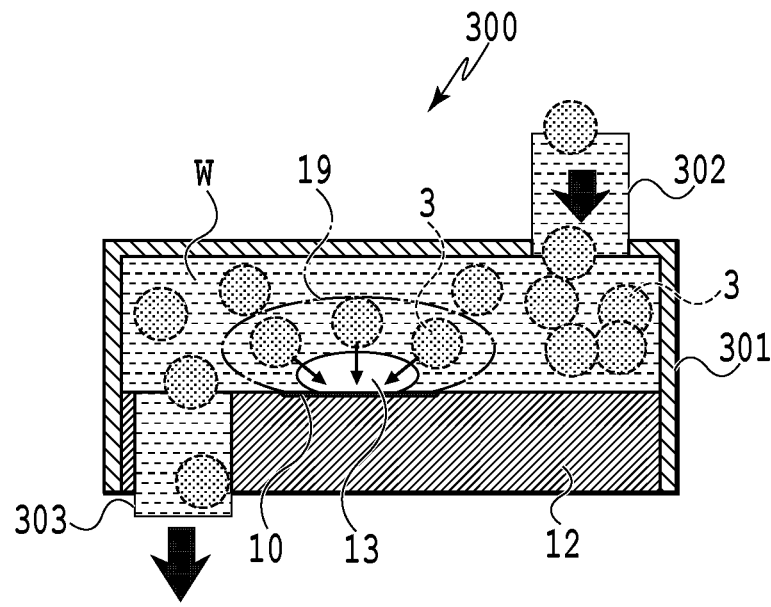
FIGS. 11A and 11B are diagrams showing how UFBs are generated by a change in saturation solubility.
Figure 11B:
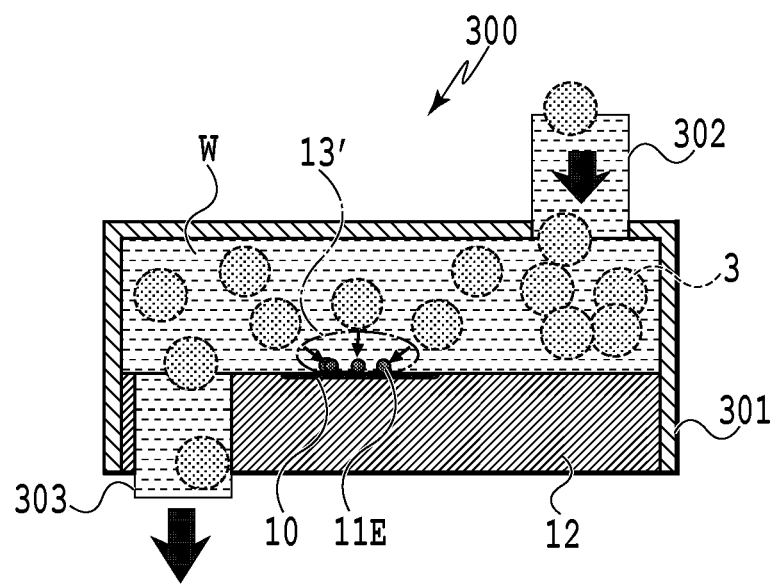

FIGS. 11A and 11B are diagrams showing how the UFBs are generated by a change in the saturation solubility of the liquid W. FIG. 11A shows a state in which the film boiling bubble 13 is generated. Along with the generation of the film boiling bubble 13, the liquid W around the film boiling bubble 13 is also heated, and a high temperature region 19 having a temperature higher than the temperature of the other region is formed around the film boiling bubble 13. As the temperature of the liquid W becomes higher, the saturation solubility of the liquid W becomes lower. Therefore, the saturation solubility of the high temperature region 19 is lower than that of the other region, and the high temperature region 19 is in an oversaturated state in which phase transition to gas is likely to occur. The gas-dissolved liquid 3 in the oversaturated state contacts the film boiling bubble 13, then causes a phase transition, becomes the UFBs, and is vaporized. In the figures, an arrow indicates a direction in which the gas-dissolved liquid 3 is vaporized. Bubbles generated by a change in the saturation solubility of the liquid around the film boiling bubble 13 in this manner are called fifth UFBs 11E.

FIG. 11B shows a state in which the film boiling bubble 13 disappears. The fifth UFBs 11E generated due to contact with the film boiling bubble 13 are attracted in the direction of the heating element 10 along with the disappearance of the film boiling bubble 13, and the liquid W fills a region 13' which was occupied by the film boiling bubble 13. Out of the vaporized UFBs, the ones which are not redissolved in the liquid W remain as the fifth UFB 11E.

As described above, it is expected that the UFBs 11 are generated in the multiple stages from the generation to the disappearance of the film boiling bubble 13 by the heat generation of the heating element 10. The first UFBs 11A, the second UFBs 11B, and the third UFBs 11C are generated near the surface of the film boiling bubble generated by the film boiling. In this case, near means a region within about 20 μm from the surface of the film boiling bubble. The fourth UFBs 11D are generated in a region through which the shock waves are propagated when the air bubble disappears. Although the above example illustrates the stages to the disappearance of the film boiling bubble 13, the way of generating the UFBs is not limited thereto. For example, with the generated film boiling bubble 13 communicating with the atmospheric air before the bubble disappearance, the UFBs can be generated also if the film boiling bubble 13 does not reach the disappearance.

Next, remaining properties of the UFBs are described. The higher the temperature of the liquid, the lower the dissolution properties of the gas components, and the lower the temperature, the higher the dissolution properties of the gas components. In other words, the phase transition of the dissolved gas components is prompted and the generation of the UFBs becomes easier as the temperature of the liquid is higher. The temperature of the liquid and the solubility of the gas are in the inverse relationship, and the gas exceeding the saturation solubility is transformed into air bubbles and appeared in the liquid as the liquid temperature increases.

Therefore, when the temperature of the liquid rapidly increases from normal temperature, the dissolution properties are decreased without stopping, and the generation of the UFBs starts. The thermal dissolution properties are decreased as the temperature increases, and a number of the UFBs are generated.

Conversely, when the temperature of the liquid decreases from normal temperature, the dissolution properties of the gas are increased, and the generated UFBs are more likely to be liquefied. However, such temperature is sufficiently lower than normal temperature. Additionally, since the once generated UFBs have a high internal pressure and large gas-liquid interface energy even when the temperature of the liquid decreases, it is highly unlikely that there is exerted a sufficiently high pressure to break such a gas-liquid interface. In other words, the once generated UFBs do not disappear easily as long as the liquid is stored at normal temperature and normal pressure.

In the above, the first UFBs 11A described with FIGS. 7A to 7C, the third UFBs 11C described with FIGS. 9A to 9C and the fifth UFBs 11E described with FIGS. 11A and 11B can be described as UFBs that are generated by utilizing such thermal dissolution properties of gas.

On the other hand, in the relationship between the pressure and the dissolution properties of liquid, the higher the pressure of the liquid, the higher the dissolution properties of the gas, and the lower the pressure, the lower the dissolution properties. In other words, the phase transition to the gas of the gas-dissolved liquid dissolved in the liquid is prompted and the generation of the UFBs becomes easier as the pressure of the liquid is lower. Once the pressure of the liquid becomes lower than normal pressure, the dissolution properties are decreased instantly, and the generation of the UFBs starts. The pressure dissolution properties are decreased as the pressure decreases, and a number of the UFBs are generated.

Conversely, when the pressure of the liquid increases to be higher than normal pressure, the dissolution properties of the gas are increased, and the generated UFBs are more likely to be liquefied. However, such pressure is sufficiently higher than the atmospheric pressure. Additionally, since the once generated UFBs have a high internal pressure and large gas-liquid interface energy even when the pressure of the liquid increases, it is highly unlikely that there is exerted a sufficiently high pressure to break such a gas-liquid interface. In other words, the once generated UFBs do not disappear easily as long as the liquid is stored at normal temperature and normal pressure.

In the above, the second UFBs 11B described with FIGS. 8A to 8C and the fourth UFBs 11D described with FIGS. 10A and 10B can be described as UFBs that are generated by utilizing such pressure dissolution properties of gas.

Those first to fourth UFBs generated by different causes are described individually above; however, the above-described generation causes occur simultaneously with the event of the film boiling. Thus, at least two types of the first to the fourth UFBs may be generated at the same time, and these generation causes may cooperate to generate the UFBs. It should be noted that it is common for all the generation causes to be induced by the volume change of the film boiling bubble generated by the film boiling phenomenon. In this specification, the method of generating the UFBs by utilizing the film boiling caused by the rapid heating as described above is referred to as a thermal-ultrafine bubble (T-UFB) generating method. Additionally, the UFBs generated by the T-UFB generating method are referred to as T-UFBs, and the liquid containing the T-UFBs generated by the T-UFB generating method is referred to as a T-UFB-containing liquid.

Almost all the air bubbles generated by the T-UFB generating method are 1.0 μm or less, and milli-bubbles and microbubbles are unlikely to be generated. That is, the T-UFB generating method allows dominant and efficient generation of the UFBs. Additionally, the T-UFBs generated by the T-UFB generating method have larger gas-liquid interface energy than that of the UFBs generated by a conventional method, and the T-UFBs do not disappear easily as long as being stored at normal temperature and normal pressure. Moreover, even if new T-UFBs are generated by new film boiling, it is possible to prevent disappearance of the already generated T-UFBs due to the impact from the new generation. That is, it can be said that the number and the concentration of the T-UFBs contained in the T-UFB-containing liquid have the hysteresis properties depending on the number of times the film boiling is made in the T-UFB-containing liquid. In other words, it is possible to adjust the concentration of the T-UFBs contained in the T-UFB-containing liquid by controlling the number of the heating elements provided in the T-UFB generating unit 300 and the number of the voltage pulse application to the heating elements.

Reference to FIG. 1 is made again. Once the T-UFB-containing liquid W with a desired UFB concentration is generated in the T-UFB generating unit 300, the UFB-containing liquid W is supplied to the post-processing unit 400.

Figure 12A:
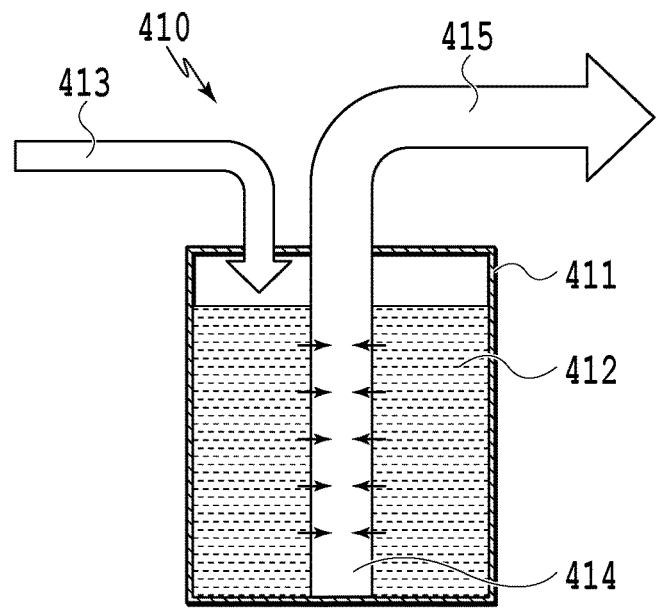
FIGS. 12A to 12C are diagrams illustrating example configurations of a post-treatment unit.
Figure 12B:
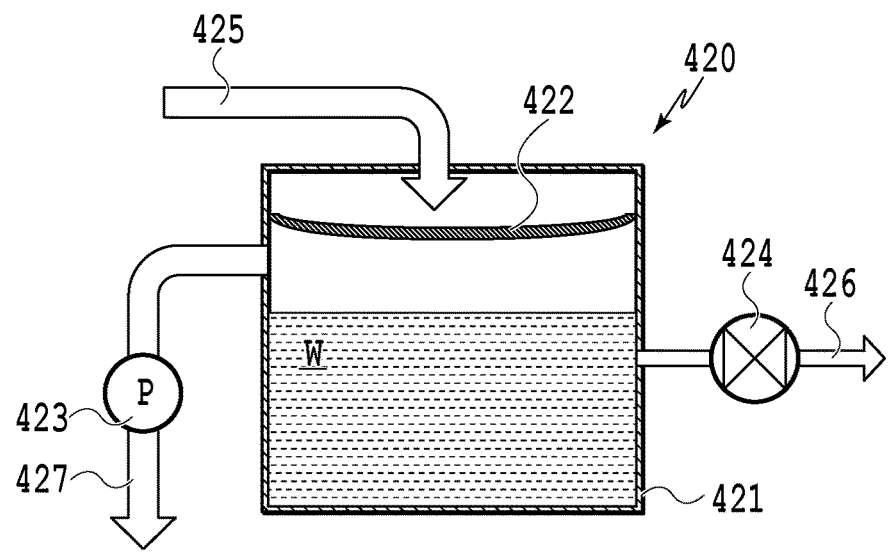
Figure 12C:
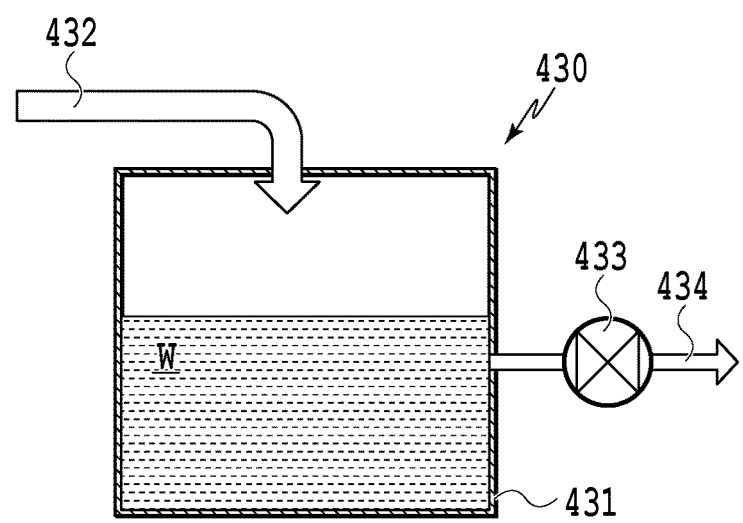

FIGS. 12A to 12C are diagrams illustrating configuration examples of the post-processing unit 400. The post-processing unit 400 removes impurities in the UFB-containing liquid W in stages in the order from inorganic ions, organic substances, and insoluble solid substances.

FIG. 12A illustrates a first post-processing mechanism 410 that removes the inorganic ions. The first post-processing mechanism 410 includes an exchange container 411, cation exchange resins 412, a liquid introduction passage 413, a collecting pipe 414, and a liquid discharge passage 415. The exchange container 411 stores the cation exchange resins 412. The UFB-containing liquid W generated by the T-UFB generating unit 300 is injected to the exchange container 411 through the liquid introduction passage 413 and absorbed into the cation exchange resins 412 such that the cations as the impurities are removed. Such impurities include metal materials peeled off from the element substrate 12 of the T-UFB generating unit 300, such as $SiO_2$, SiN, SiC, Ta, $Al_2O_3$, $Ta_2O_5$, and Ir.

The cation exchange resins 412 are synthetic resins in which a functional group (ion exchange group) is introduced in a high polymer matrix having a three-dimensional network, and the appearance of the synthetic resins are spherical particles of around 0.4 to 0.7 mm. A general high polymer matrix is the styrene-divinylbenzene copolymer, and the functional group may be that of methacrylic acid series and acrylic acid series, for example. However, the above material is an example. As long as the material can remove desired inorganic ions effectively, the above material can be changed to various materials. The UFB-containing liquid W absorbed in the cation exchange resins 412 to remove the inorganic ions is collected by the collecting pipe 414 and transferred to the next step through the liquid discharge passage 415. In this process, not all the inorganic ions contained in the UFB-containing liquid W supplied from the liquid introduction passage 413 need to be removed as long as at least a part of the inorganic ions are removed.

FIG. 12B illustrates a second post-processing mechanism 420 that removes the organic substances. The second post-processing mechanism 420 includes a storage container 421, a filtration filter 422, a vacuum pump 423, a valve 424, a liquid introduction passage 425, a liquid discharge passage 426, and an air suction passage 427. Inside of the storage container 421 is divided into upper and lower two regions by the filtration filter 422. The liquid introduction passage 425 is connected to the upper region of the upper and lower two regions, and the air suction passage 427 and the liquid discharge passage 426 are connected to the lower region thereof. Once the vacuum pump 423 is driven with the valve 424 closed, the air in the storage container 421 is discharged through the air suction passage 427 to make the pressure inside the storage container 421 negative pressure, and the UFB-containing liquid W is thereafter introduced from the liquid introduction passage 425. Then, the UFB-containing liquid W from which the impurities are removed by the filtration filter 422 is reserved into the storage container 421.

The impurities removed by the filtration filter 422 include organic materials that may be mixed at a tube or each unit, such as organic compounds including silicon, siloxane, and epoxy, for example. A filter film usable for the filtration filter 422 includes a filter of a sub-µm-mesh (a filter of 1 µm or smaller in mesh diameter) that can remove bacteria, and a filter of a nm-mesh that can remove virus. The filtration filter having such a fine opening diameter may remove air bubbles larger than the opening diameter of the filter. Particularly, there may be the case where the filter is clogged by the fine air bubbles adsorbed to the openings (mesh) of the filter, which may slowdown the filtering speed. However, as described above, most of the air bubbles generated by the T-UFB generating method described in the present embodiment of the invention are in the size of 1 µm or smaller in diameter, and milli-bubbles and microbubbles are not likely to be generated. That is, since the probability of generating milli-bubbles and microbubbles is extremely low, it is possible to suppress the slowdown in the filtering speed due to the adsorption of the air bubbles to the filter. For this reason, it is favorable to apply the filtration filter 422 provided with the filter of 1 µm or smaller in mesh diameter to the system having the T-UFB generating method.

Examples of the filtration applicable to this embodiment may be a so-called dead-end filtration and cross-flow filtration. In the dead-end filtration, the direction of the flow of the supplied liquid and the direction of the flow of the filtration liquid passing through the filter openings are the same, and specifically, the directions of the flows are made along with each other. In contrast, in the cross-flow filtration, the supplied liquid flows in a direction along a filter surface, and specifically, the direction of the flow of the supplied liquid and the direction of the flow of the filtration liquid passing through the filter openings are crossed with each other. It is preferable to apply the cross-flow filtration to suppress the adsorption of the air bubbles to the filter openings.

After a certain amount of the UFB-containing liquid W is reserved in the storage container 421, the vacuum pump 423 is stopped and the valve 424 is opened to transfer the T-UFB-containing liquid in the storage container 421 to the next step through the liquid discharge passage 426. Although the vacuum filtration method is employed as the method of removing the organic impurities herein, a gravity filtration method and a pressurized filtration can also be employed as the filtration method using a filter, for example.

FIG. 12C illustrates a third post-processing mechanism 430 that removes the insoluble solid substances. The third post-processing mechanism 430 includes a precipitation container 431, a liquid introduction passage 432, a valve 433, and a liquid discharge passage 434.

First, a predetermined amount of the UFB-containing liquid W is reserved into the precipitation container 431 through the liquid introduction passage 432 with the valve 433 closed, and leaving it for a while. Meanwhile, the solid substances in the UFB-containing liquid W are precipitated onto the bottom of the precipitation container 431 by gravity. Among the bubbles in the UFB-containing liquid, relatively large bubbles such as microbubbles are raised to the liquid surface by the buoyancy and also removed from the UFB-containing liquid. After a lapse of sufficient time, the valve 433 is opened, and the UFB-containing liquid W from which the solid substances and large bubbles are removed is transferred to the collecting unit 500 through the liquid discharge passage 434. The example of applying the three post-processing mechanisms in sequence is shown; however, it is not limited thereto, and the order of the three post-processing mechanisms may be changed, or at least one needed post-processing mechanism may be employed.

Reference to FIG. 1 is made again. The T-UFB-containing liquid W from which the impurities are removed by the post-processing unit 400 may be directly transferred to the collecting unit 500 or may be put back to the dissolving unit 200 again. In the latter case, the gas dissolution concentration of the T-UFB-containing liquid W that is decreased due to the generation of the T-UFBs can be compensated to the saturated state again by the dissolving unit 200. If new T-UFBs are generated by the T-UFB generating unit 300 after the compensation, it is possible to further increase the concentration of the UFBs contained in the T-UFB-containing liquid with the above-described properties. That is, it is possible to increase the concentration of the contained UFBs by the number of circulations through the dissolving unit 200, the T-UFB generating unit 300, and the post-processing unit 400, and it is possible to transfer the UFB-containing liquid W to the collecting unit 500 after a predetermined concentration of the contained UFBs is obtained. The above example shows a form in which the UFB-containing liquid processed by the post-processing unit 400 is put back to the dissolving unit 200 and circulated; however, it is not limited thereto, and the UFB-containing liquid after passing through the T-UFB generating unit may be put back again to the dissolving unit 200 before being supplied to the post-processing unit 400 such that the post-processing is performed by the post-processing unit 400 after the T-UFB concentration is increased through multiple times of circulation, for example.

The collecting unit 500 collects and preserves the UFB-containing liquid W transferred from the post-processing unit 400. The T-UFB-containing liquid collected by the collecting unit 500 is a UFB-containing liquid with high purity from which various impurities are removed.

In the collecting unit 500, the UFB-containing liquid W may be classified by the size of the T-UFBs by performing some stages of filtration processing. Since it is expected that the temperature of the T-UFB-containing liquid W obtained by the T-UFB method is higher than normal temperature, the collecting unit 500 may be provided with a cooling unit. The cooling unit may be provided to a part of the post-processing unit 400.

The schematic description of the UFB generating apparatus 1 is given above; however, it is needless to say that the illustrated multiple units can be changed, and not all of them need to be prepared. Depending on the type of the liquid W and the gas G to be used and the intended use of the T-UFB-containing liquid to be generated, a part of the above-described units may be omitted, or another unit other than the above-described units may be added.

For example, when the gas to be contained by the UFBs is the atmospheric air, the degassing unit as the pre-processing unit 100 and the dissolving unit 200 can be omitted. On the other hand, when multiple kinds of gases are desired to be contained by the UFBs, another dissolving unit 200 may be added.

The units for removing the impurities as described in FIGS. 12A to 12C may be provided upstream of the T-UFB generating unit 300 or may be provided both upstream and downstream thereof. When the liquid to be supplied to the UFB generating apparatus is tap water, rain water, contaminated water, or the like, there may be included organic and inorganic impurities in the liquid. If such a liquid W including the impurities is supplied to the T-UFB generating unit 300, there is a risk of deteriorating the heating element 10 and inducing the salting-out phenomenon. With the mechanisms as illustrated in FIGS. 12A to 12C provided upstream of the T-UFB generating unit 300, it is possible to remove the above-described impurities previously.

<<Liquid and Gas Usable for T-UFB-Containing Liquid>>

Now, the liquid W usable for generating the T-UFB-containing liquid is described. The liquid W usable is, for example, pure water, ion exchange water, distilled water, bioactive water, magnetic active water, lotion, tap water, sea water, river water, clean and sewage water, lake water, underground water, rain water, and so on. A mixed liquid containing the above liquid and the like is also usable. A mixed solvent containing water and soluble organic solvent can be also used. The soluble organic solvent to be used by being mixed with water is not particularly limited; however, the followings can be a specific example thereof. An alkyl alcohol group of the carbon number of 1 to 4 including methyl alcohol, ethyl alcohol, n-propyl alcohol, isopropyl alcohol, n-butyl alcohol, sec-butyl alcohol, and tert-butyl alcohol. An amide group including N-methyl-2-pyrrolidone, 2-pyrrolidone, 1,3-dimethyl-2-imidazolidinone, N,N-dimethylformamide, and N,N-dimethylacetamide. A keton group or a ketoalcohol group including acetone and diacetone alcohol. A cyclic ether group including tetrahydrofuran and dioxane. A glycol group including ethylene glycol, 1,2-propylene glycol, 1,3-propylene glycol, 1,2-butanediol, 1,3-butanediol, 1,4-butanediol, 1,5-pentanediol, 1,2-hexanediol, 1,6-hexanediol, 3-methyl-1,5-pentanediol, diethylene glycol, triethylene glycol, and thiodiglycol. A group of lower alkyl ether of polyhydric alcohol including ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, and triethylene glycol monobutyl ether. A polyalkylene glycol group including polyethylene glycol and polypropylene glycol. A triol group including glycerin, 1,2,6-hexanetriol, and trimethylolpropane. These soluble organic solvents can be used individually, or two or more of them can be used together.

A gas component that can be introduced into the dissolving unit 200 is, for example, hydrogen, helium, oxygen, nitrogen, methane, fluorine, neon, carbon dioxide, ozone, argon, chlorine, ethane, propane, air, and so on. The gas component may be a mixed gas containing some of the above. Additionally, it is not necessary for the dissolving unit 200 to dissolve a substance in a gas state, and the dissolving unit 200 may fuse a liquid or a solid containing desired components into the liquid W. The dissolution in this case may be spontaneous dissolution, dissolution caused by pressure application, or dissolution caused by hydration, ionization, and chemical reaction due to electrolytic dissociation.

<<Effects of T-UFB Generating Method>>

Next, the characteristics and the effects of the above-described T-UFB generating method are described by comparing with a conventional UFB generating method. For example, in a conventional air bubble generating apparatus as represented by the Venturi method, a mechanical depressurizing structure such as a depressurizing nozzle is provided in a part of a flow passage. A liquid flows at a predetermined pressure to pass through the depressurizing structure, and air bubbles of various sizes are generated in a downstream region of the depressurizing structure.

In this case, among the generated air bubbles, since the relatively large bubbles such as milli-bubbles and microbubbles are affected by the buoyancy, such bubbles rise to the liquid surface and disappear. Even the UFBs that are not affected by the buoyancy may also disappear with the milli-bubbles and microbubbles since the gas-liquid interface energy of the UFBs is not very large. Additionally, even if the above-described depressurizing structures are arranged in series, and the same liquid flows through the depressurizing structures repeatedly, it is impossible to store for a long time the UFBs of the number corresponding to the number of repetitions. In other words, it has been difficult for the UFB-containing liquid generated by the conventional UFB generating method to maintain the concentration of the contained UFBs at a predetermined value for a long time.

In contrast, in the T-UFB generating method utilizing the film boiling, a rapid temperature change from normal temperature to about 300° C. and a rapid pressure change from normal pressure to around a several megapascal occur locally in a part extremely close to the heating element. The heating element is a rectangular shape having one side of around several tens to hundreds of m. It is around 1/10 to 1/1000 of the size of a conventional UFB generating unit. Additionally, with the gas-dissolved liquid within the extremely thin film region of the film boiling bubble surface exceeding the thermal dissolution limit or the pressure dissolution limit instantaneously (in an extremely short time under microseconds), the phase transition occurs and the gas-dissolved liquid is precipitated as the UFBs. In this case, the relatively large bubbles such as milli-bubbles and microbubbles are hardly generated, and the liquid contains the UFBs of about 100 nm in diameter with extremely high purity. Moreover, since the T-UFBs generated in this way have sufficiently large gas-liquid interface energy, the T-UFBs are not broken easily under the normal environment and can be stored for a long time.

Particularly, the present invention using the film boiling phenomenon that enables local formation of a gas interface in the liquid can form an interface in a part of the liquid close to the heating element without affecting the entire liquid region, and a region on which the thermal and pressure actions performed can be extremely local. As a result, it is possible to stably generate desired UFBs. With further more conditions for generating the UFBs applied to the generation liquid through the liquid circulation, it is possible to additionally generate new UFBs with small effects on the already-made UFBs. As a result, it is possible to produce a UFB liquid of a desired size and concentration relatively easily.

Moreover, since the T-UFB generating method has the above-described hysteresis properties, it is possible to increase the concentration to a desired concentration while keeping the high purity. In other words, according to the T-UFB generating method, it is possible to efficiently generate a long-time storable UFB-containing liquid with high purity and high concentration.

<<Specific Usage of T-UFB-Containing Liquid>>

In general, applications of the ultrafine bubble-containing liquids are distinguished by the type of the containing gas. Any type of gas can make the UFBs as long as an amount of around PPM to BPM of the gas can be dissolved in the liquid. For example, the ultrafine bubble-containing liquids can be applied to the following applications.

A UFB-containing liquid containing air can be preferably applied to cleansing in the industrial, agricultural and fishery, and medical scenes and the like, and to cultivation of plants and agricultural and fishery products.

A UFB-containing liquid containing ozone can be preferably applied to not only cleansing application in the industrial, agricultural and fishery, and medical scenes and the like, but to also applications intended to disinfection, sterilization, and decontamination, and environmental cleanup of drainage and contaminated soil, for example.

A UFB-containing liquid containing nitrogen can be preferably applied to not only cleansing application in the industrial, agricultural and fishery, and medical scenes and the like, but to also applications intended to disinfection, sterilization, and decontamination, and environmental cleanup of drainage and contaminated soil, for example.

A UFB-containing liquid containing oxygen can be preferably applied to cleansing application in the industrial, agricultural and fishery, and medical scenes and the like, and to cultivation of plants and agricultural and fishery products.

A UFB-containing liquid containing carbon dioxide can be preferably applied to not only cleansing application in the industrial, agricultural and fishery, and medical scenes and the like, but to also applications intended to disinfection, sterilization, and decontamination, for example.

A UFB-containing liquid containing perfluorocarbons as a medical gas can be preferably applied to ultrasonic diagnosis and treatment. As described above, the UFB-containing liquids can exert the effects in various fields of medical, chemical, dental, food, industrial, agricultural and fishery, and so on.

In each of the applications, the purity and the concentration of the UFBs contained in the UFB-containing liquid are important for quickly and reliably exert the effect of the UFB-containing liquid. In other words, unprecedented effects can be expected in various fields by utilizing the T-UFB generating method that enables generation of the UFB-containing liquid with high purity and desired concentration. Here is below a list of the applications in which the T-UFB generating method and the T-UFB-containing liquid are expected to be preferably applicable.

(A) Liquid Purification Application

With the T-UFB generating unit provided to a water clarification unit, enhancement of an effect of water clarification and an effect of purification of PH adjustment liquid is expected. The T-UFB generating unit may also be provided to a carbonated water server.

With the T-UFB generating unit provided to a humidifier, aroma diffuser, coffee maker, and the like, enhancement of a humidifying effect, a deodorant effect, and a scent spreading effect in a room is expected.

If the UFB-containing liquid in which an ozone gas is dissolved by the dissolving unit is generated and is used for dental treatment, burn treatment, and wound treatment using an endoscope, enhancement of a medical cleansing effect and an antiseptic effect is expected.

With the T-UFB generating unit provided to a water storage tank of a condominium, enhancement of a water clarification effect and chlorine removing effect of drinking water to be stored for a long time is expected.

If the T-UFB-containing liquid containing ozone or carbon dioxide is used for brewing process of Japanese sake, shochu, wine, and so on in which the high-temperature pasteurization processing cannot be performed, more efficient pasteurization processing than that with the conventional liquid is expected.

If the UFB-containing liquid is mixed into the ingredient in a production process of the foods for specified health use and the foods with functional claims, the pasteurization processing is possible, and thus it is possible to provide safe and functional foods without a loss of flavor.

With the T-UFB generating unit provided to a supplying route of sea water and fresh water for cultivation in a cultivation place of fishery products such as fish and pearl, prompting of spawning and growing of the fishery products is expected.

With the T-UFB generating unit provided in a purification process of water for food preservation, enhancement of the preservation state of the food is expected.

With the T-UFB generating unit provided in a bleaching unit for bleaching pool water or underground water, a higher bleaching effect is expected.

With the T-UFB-containing liquid used for repairing a crack of a concrete member, enhancement of the effect of crack repairment is expected.

With the T-UFBs contained in liquid fuel for a machine using liquid fuel (such as automobile, vessel, and airplane), enhancement of energy efficiency of the fuel is expected.

(B) Cleansing Application

Recently, the UFB-containing liquids have been receiving attention as cleansing water for removing soils and the like attached to clothing. If the T-UFB generating unit described in the above embodiment is provided to a washing machine, and the UFB-containing liquid with higher purity and better permeability than the conventional liquid is supplied to the washing tub, further enhancement of detergency is expected.

With the T-UFB generating unit provided to a bath shower and a bedpan washer, not only a cleansing effect on all kinds of animals including human body but also an effect of prompting contamination removal of a water stain and a mold on a bathroom and a bedpan are expected.

With the T-UFB generating unit provided to a window washer for automobiles, a high-pressure washer for cleansing wall members and the like, a car washer, a dishwasher, a food washer, and the like, further enhancement of the cleansing effects thereof is expected.

With the T-UFB-containing liquid used for cleansing and maintenance of parts produced in a factory including a burring step after pressing, enhancement of the cleansing effect is expected.

In production of semiconductor elements, if the T-UFB-containing liquid is used as polishing water for a wafer, enhancement of the polishing effect is expected. Additionally, if the T-UFB-containing liquid is used in a resist removal step, prompting of peeling of resist that is not peeled off easily is enhanced.

With the T-UFB generating unit is provided to machines for cleansing and decontaminating medical machines such as a medical robot, a dental treatment unit, an organ preservation container, and the like, enhancement of the cleansing effect and the decontamination effect of the machines is expected. The T-UFB generating unit is also applicable to treatment of animals.

(C) Pharmaceutical Application

If the T-UFB-containing liquid is contained in cosmetics and the like, permeation into subcutaneous cells is prompted, and additives that give bad effects to skin such as preservative and surfactant can be reduced greatly. As a result, it is possible to provide safer and more functional cosmetics.

If a high concentration nanobubble preparation containing the T-UFBs is used for contrasts for medical examination apparatuses such as a CT and an MRI, reflected light of X-rays and ultrasonic waves can be efficiently used. This makes it possible to capture a more detailed image that is usable for initial diagnosis of a cancer and the like.

If a high concentration nanobubble water containing the T-UFBs is used for a ultrasonic wave treatment machine called high-intensity focused ultrasound (HIFU), the irradiation power of ultrasonic waves can be reduced, and thus the treatment can be made more non-invasive. Particularly, it is possible to reduce the damage to normal tissues.

It is possible to create a nanobubble preparation by using high concentration nanobubbles containing the T-UFBs as a source, modifying a phospholipid forming a liposome in a negative electric charge region around the air bubble, and applying various medical substances (such as DNA and RNA) through the phospholipid.

If a drug containing high concentration nanobubble water made by the T-UFB generation is transferred into a dental canal for regenerative treatment of pulp and dentine, the drug enters deeply a dentinal tubule by the permeation effect of the nanobubble water, and the decontamination effect is prompted. This makes it possible to treat the infected root canal of the pulp safely in a short time.

First Embodiment

Figure 13:
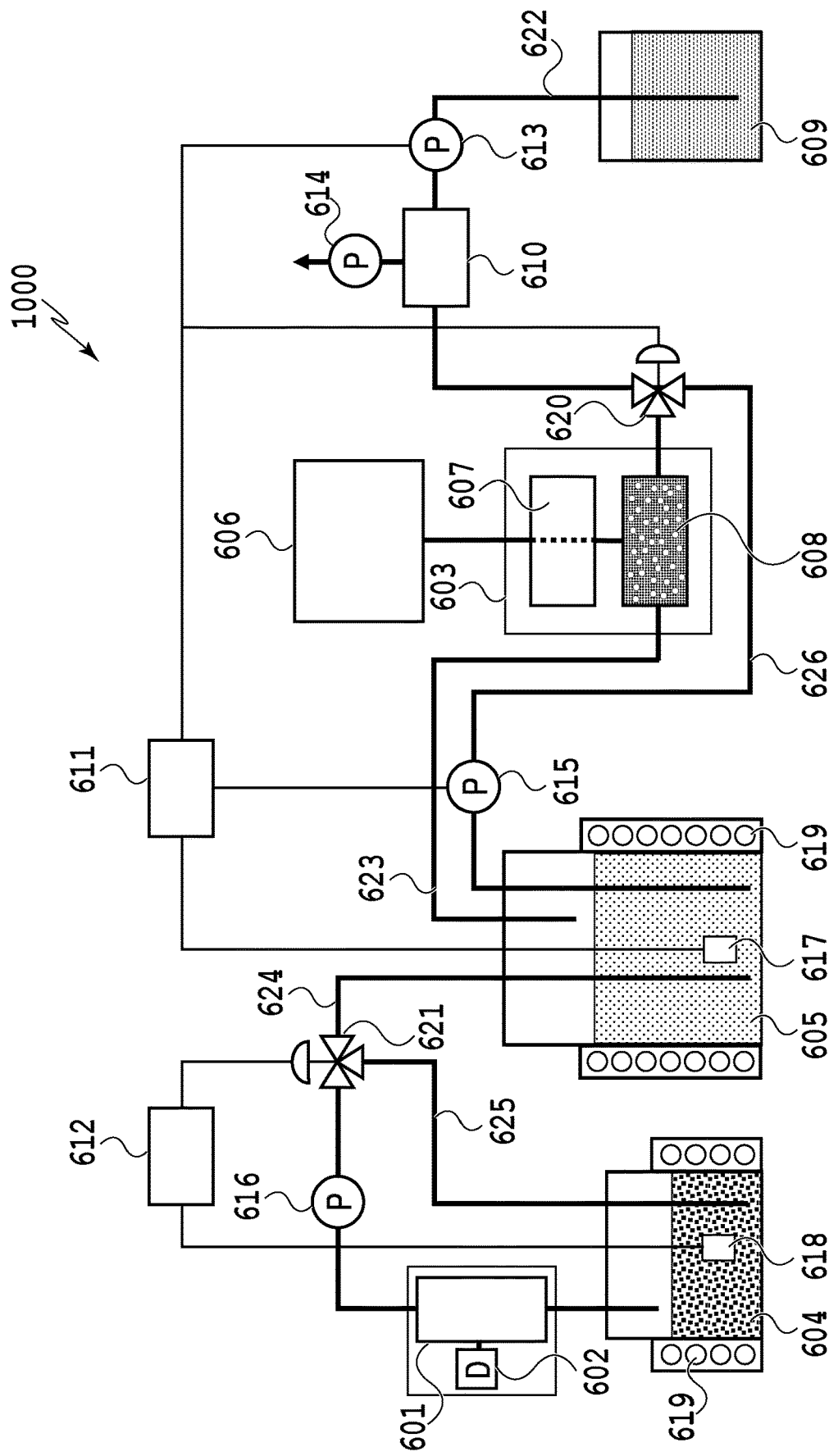
FIG. 13 is a diagram showing the arrangement of units in an ozone UFB generating apparatus.

FIG. 13 is a diagram showing the arrangement of units in an ozone ultrafine bubble generating apparatus (hereinafter referred to as a UFB generating apparatus) 1000 used in a first embodiment. Pure water accumulated in a pure water supply reservoir 609 is fed to a degassing module 610 by a pure water feed pump 613 through pure water supply piping 622. In the degassing module 610, a gas mixed in the pure water is removed by a degassing pump 614. The degassed pure water is supplied to an ozone water generator 603 through a three-way valve 620. The degassing module 610 in FIG. 13 corresponds to the pretreatment unit 100 in FIG. 1.

The ozone water generator 603 has an ozone generator 607 and an ozone dissolution tank 608. The ozone generator 607 generates ozone $O_3$ by performing treatments such as plasma discharge on oxygen $O_2$ supplied from an oxygen concentrator 606. The ozone dissolution tank 608 generates ozone water by dissolving the ozone supplied from the ozone generator 607 into the pure water flowing in from the three-way valve 620.

The ozone water generated by the ozone water generator 603 is accumulated in an ozone water accumulation reservoir 605 through first ozone water supply piping 623. An ozone water concentration sensor 617 is placed in the ozone water accumulation reservoir 605 to measure the concentration of ozone in the ozone water, and the concentration detected by the ozone water concentration sensor 617 is sent to an ozone water concentration control unit 611. In a case where the detected concentration is below a predetermined value, the ozone water concentration control unit 611 drives a circulation pump 615, switches the three-way valve 620, and supplies the ozone water accumulated in the ozone water accumulation reservoir 605 back to the ozone water generator 603 through ozone water circulation piping 626.

In this way, the ozone water concentration control unit 611 controls the pure water feed pump 613, the three-way valve 620, and the circulation pump 615 while checking the concentration detected by the ozone water concentration sensor 617. In other words, the ozone water concentration control unit 611 supplies a predetermined amount of pure water from the pure water supply reservoir 609 to the ozone dissolution tank 608, and then circulates ozone water between the ozone water accumulation reservoir 605 and the ozone water generator 603 until a desired concentration is detected. According to the study done by the inventors of the present invention, ozone water with a concentration of 40 ppm could be generated from approximately 20 litters of pure water in approximately 15 minutes. The functions of the ozone water generator 603 and the ozone water accumulation reservoir 605 in FIG. 13 correspond to the dissolving unit 200 in FIG. 1.

As shown in FIG. 13, the ozone water accumulation reservoir 605 may be covered with a cooling jacket 619 to keep ozone water between 10° C. and 15° C. Then, gasification of ozone can be suppressed, and ozone water with a desired concentration can be generated in a shorter period of time.

After ozone water with a desired concentration is obtained, the ozone water accumulated in the ozone water accumulation reservoir 605 is supplied to an ultrafine bubble generating head (hereinafter referred to as a UFB generating head) 601 by an ozone water feed pump 616 through second ozone water supply piping 624. The UFB generating head 601 corresponds to the chamber 301 depicted in FIG. 4, and has an element substrate on which a plurality of heating elements are arranged. The UFB generating head 601 is driven by a head driver 602, and generates ozone UFBs in the ozone water supplied thereto, according to the mechanism depicted in FIGS. 7A to 11B. A UFB-contained liquid containing ozone UFBs flowing from the UFB generating head 601 is accumulated in a UFB-contained liquid collecting reservoir 604.

A UFB concentration sensor 618 is placed in the UFB-contained liquid collecting reservoir 604 to measure the concentration of ozone UFBs in the UFB-contained liquid, and the concentration detected by the UFB concentration sensor 618 is sent to a UFB concentration control unit 612. In a case where the detected concentration is below a predetermined value, the UFB concentration control unit 612 switches a three-way valve 621 so that the ozone water feed pump 616 may be fluidly connected to UFB-contained liquid circulation piping 625, and drives the ozone water feed pump 616. Thereby, a circulation flow channel is formed for circulation between the UFB-contained liquid collecting reservoir 604 and the UFB generating head 601, to be able to gradually increase the concentration of ozone UFBs in the UFB-contained liquid accumulated in the UFB-contained liquid collecting reservoir 604.

In other words, the UFB concentration control unit 612 controls the ozone water feed pump 616 and the three-way valve 621 while checking the concentration detected by the UFB concentration sensor 618. Then, the UFB concentration control unit 612 circulates the ozone water between the UFB-contained liquid collecting reservoir 604 and the UFB generating head 601 until a desired UFB concentration is detected.

The UFB-contained liquid collecting reservoir 604 is covered with a cooling jacket 619 to keep the temperature of the accumulated ozone water low. Keeping the ozone UFB-contained liquid in the UFB-contained liquid collecting reservoir 604 at low temperature helps suppress gasification of ozone and stabilize the concentration of ozone UFBs. The functions of the UFB generating head 601 and the UFB-contained liquid collecting reservoir 604 described above correspond to the T-UFB generating unit 300 in FIG. 1.

In a system that circulates ozone water like in the present embodiment, there is a concern of corrosion of a material of a member, such as piping, that comes into contact with ozone water, which has strong oxidizing power. Once the material corrodes, it is difficult to continue the operation of the apparatus, requiring more frequent maintenance and therefore more running costs. Moreover, the corroded and deteriorated material may be dissolved into a UFB-contained liquid and be mixed therein as impurities, degrading the purity of and in turn the quality of the ozone UFB-contained liquid generated.

Thus, in the UFB generating apparatus 1000 of the present embodiment, a material that is particularly unlikely to corrode due to oxidation (i.e., a corrosion-resistant material) is selected for the members assembled. For example, a tube made of stainless steel (SUS 316) or perfluoroalkoxy alkanes (PFA), which is a fluororesin, is used for the ozone water circulation piping 626 and the UFB-contained liquid circulation piping 625. Polytetrafluoroethylene (PTFE) is used for joints and the three-way valves 620, 621 that couple a unit and piping. A diaphragm pump made of PTFE (Smoothflow Pump manufactured by TACMINA CORPORATION) is used for the circulation pump 615 and the ozone water feed pump 616. PFA is used for the ozone water accumulation reservoir 605 and the UFB-contained liquid collecting reservoir 604. In this way, the present embodiment uses materials with high oxidation resistance to form the units.

Next, a detailed description is given of the configuration of the UFB generating head 601 with excellent oxidation resistance used in the present embodiment.

Figure 14:
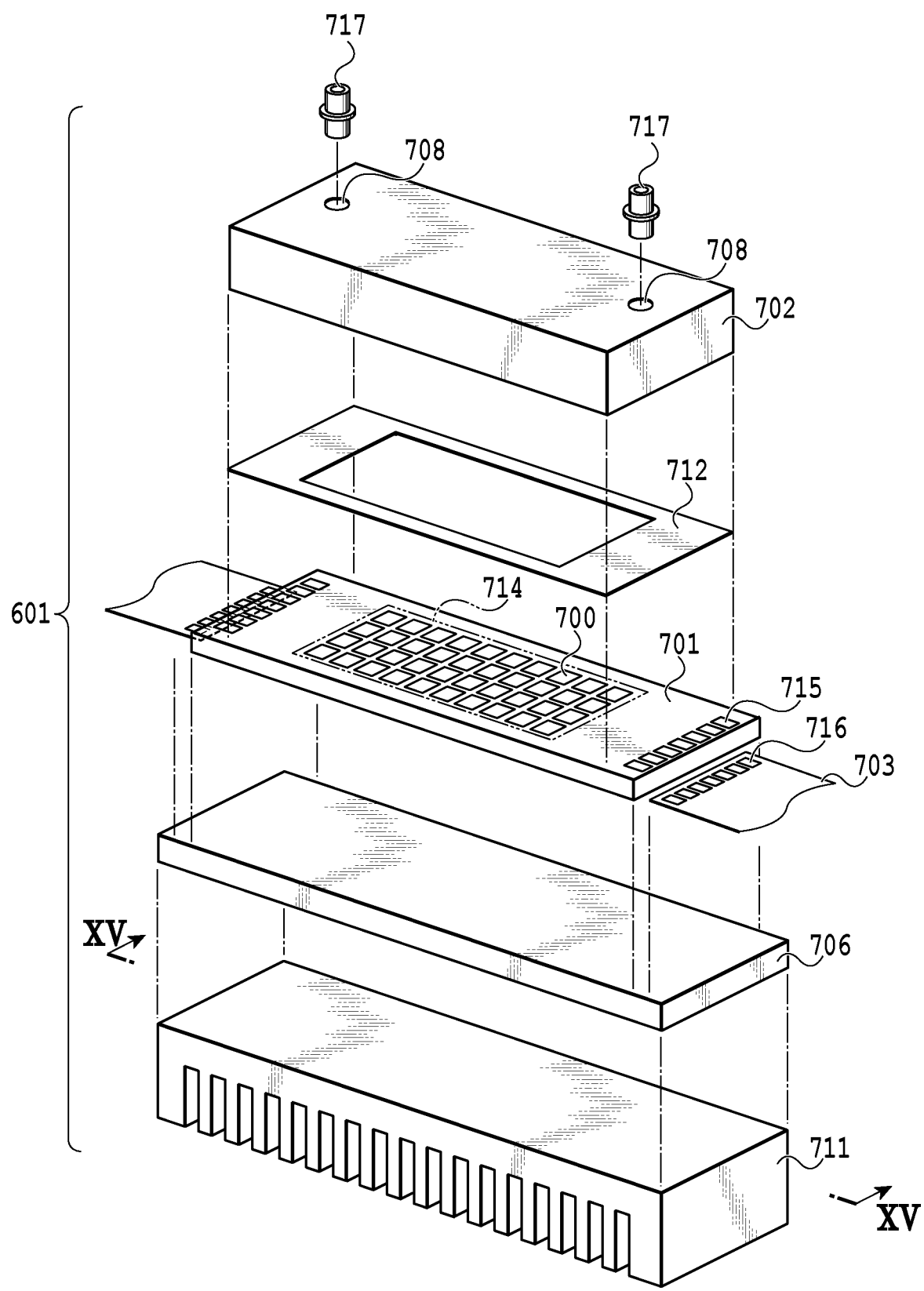
FIG. 14 is an exploded perspective view of a UFB generating head of a first embodiment.
Figure 15A:
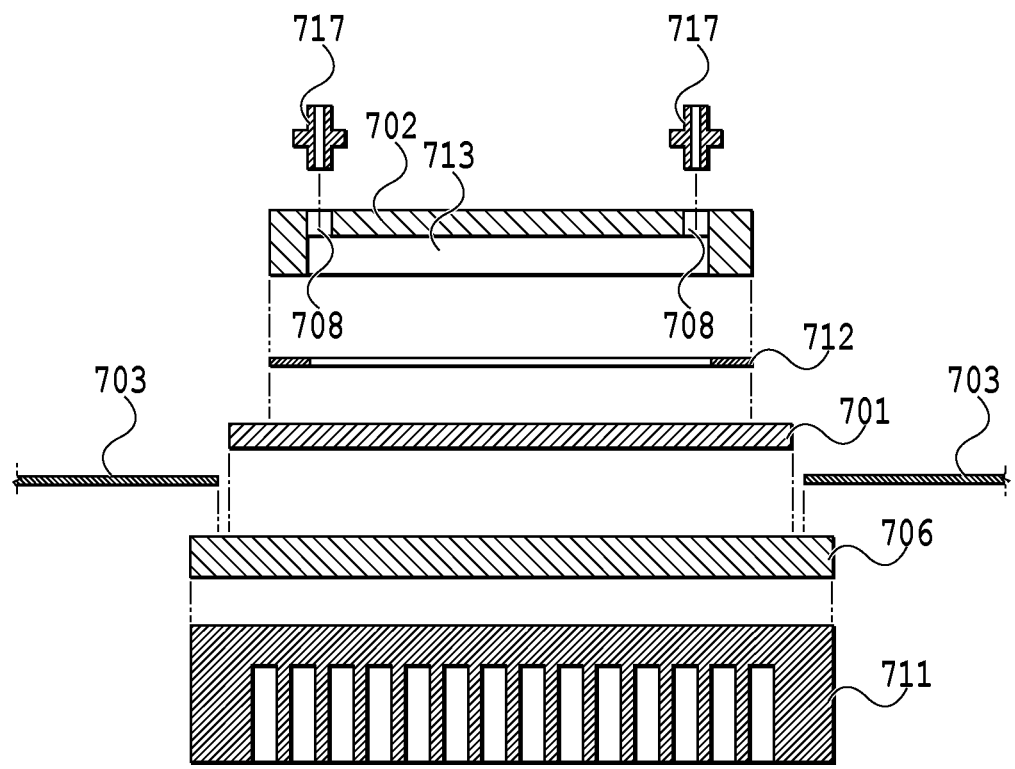
FIGS. 15A and 15B are sectional views of the UFB generating head of the first embodiment.
Figure 15B:
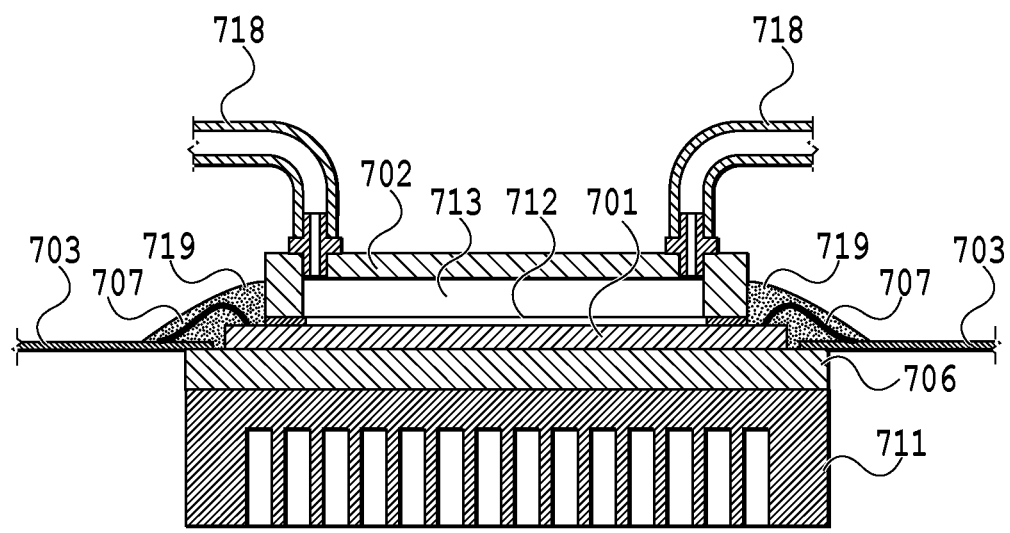

FIG. 14 is an exploded perspective view illustrating the configuration of the UFB generating head 601 used in the present embodiment. FIG. 15A is a sectional view of FIG. 14, and FIG. 15B is a sectional view of the UFB generating head 601.

The UFB generating head 601 of the present embodiment is formed by a heat dissipation plate 711, a support substrate 706, an element substrate 701, a seal member 712, and a flow channel member 702 which are stacked in this order. A plurality of heating elements 700 that generate heat upon application of voltage thereto are arranged on an elements-arranged area 714 of the element substrate 701. The box-shaped flow channel member 702 is bonded to the element substrate 701 while facing the elements-arranged area 714. Thereby, a space is formed between the flow channel member 702 and the elements-arranged area 714, serving as a liquid flow channel 713.

The flow channel member 702 has through-holes 708 which are formed at end portions thereof in the longitudinal direction and penetrate thereinto. Joints 717 are fitted into these through-holes 708, and tubes 718 (not shown in FIG. 14) can be connected to the joints 717. In such a configuration, a flow channel is formed which starts from one of the joints 717, extends through the liquid flow channel 713, and connects to the other one of the joints 717.

A brief description is given below of a method of manufacturing the UFB generating head 601 of the present embodiment. First, a predetermined semiconductor process is performed on an eight-inch silicon substrate to form 60 element substrate structures on the silicon substrate. Each element substrate structure measures 22 mm×17 mm and includes components such as the heating elements 700 and substrate-side electrodes 715 for receiving drive signals for the heating elements 700. An anti-cavitation film 310 with high corrosion resistance is formed on the surface of each element substrate structure, considering not only chemical and physical impact caused by heat generated by the heating elements 700, but also contact with ozone water (see FIGS. 5A and 5B). To enhance particularly corrosion resistance to ozone water like in the present embodiment, it is preferable that the anti-cavitation film 310 contains tantalum, iridium, titanium (Ti, $TiO_2$), or the like. After such element substrate structures are formed, the silicon substrate is cut and separated into 60 element substrates 701 using a dicing apparatus.

Next, one of the element substrates 701 thus fabricated is bonded to the support substrate 706 made of alumina ceramics. The substrate-side electrodes 715 placed on both sides of the element substrate 701 are connected to wiring substrate-side electrodes 716 placed at end portions of flexible wiring substrates 703 with wire bonding 707 using gold wires with a diameter of 25 microns. The element substrate 701 and the flexible wiring substrates 703 are bonded to the support substrate 706 made of alumina ceramics using a thermosetting epoxy adhesive (E3210 manufactured by Henkel Japan Ltd.) or the like.

Next, the flow channel member 702 made of stainless steel (SUS 316) is mounted onto the element substrate 701 with the seal member 712 interposed therebetween. The seal member 712 is 0.05 mm thick and made of PTFE. The flow channel member 702 has the liquid flow channel 713 mechanically engraved therein, and the through-holes 708 are formed at portions to be the inlet and outlet of liquid. The flow channel member 702 is mounted at a position which includes the elements-arranged area 714 but does not include the substrate-side electrodes 715. In other words, the substrate-side electrodes 715 are located outside the flow channel member 702. Thereafter, a cold-setting silicone sealer 719 (TSE 399 manufactured by Momentive Performance Materials Inc.) is applied to the outer periphery of the flow channel member 702, thereby fixing the flow channel member 702 to the support substrate 706.

Although stainless steel (SUS 316) is used for the flow channel member in the present embodiment, the material is not limited to this as long as the material is corrosion-resistant to ozone water, and may be PTFE or glass. Glass in particular makes the situation inside the flow channel observable, and thus makes it possible to check for the presence of large bubbles that inhibit the flow of liquid and generation of UFBs and to thereby find the right time for recovery operation. With regards to glass, borosilicate glass (such as Pyrex (registered trademark)) is highly corrosion-resistant to ozone water and is therefore suitable for the flow channel member. Quartz may be used instead.

Although a thermosetting epoxy adhesive is used for the bonding of the element substrate and a silicon resin is used as a sealer to seal the periphery, it is more reliable to use a hardened material (fluororesin) of a liquid fluorinated elastomer (SIFEL2000 series manufactured by Shin-Etsu Chemical Co., Ltd.) which is more corrosion resistant to ozone water.

The seal member 712 acts as a protective layer that helps prevent damage to the surface of the element substrate 701 caused by the contact of the flow channel member 702 made of SUS 316 with the element substrate 701, and also prevent the silicone sealer 719 from being exposed to the liquid flow channel 713. Generally, in a case of manufacturing the element substrate 701 using a semiconductor process, such a protective layer is formed by a photosensitive resin using photolithography. However, in a case where ozone water flows through the liquid flow channel 713 like in the present embodiment, a photosensitive resin is likely to corrode and deteriorate due to the strong oxidizing power of ozone water. For this reason, the seal member 712 cut out from a sheet made of PTFE, which has high oxidation resistance (i.e., high corrosion resistance to ozone water), is used as the protective layer in the present embodiment.

Next, the joints 717 made of polytetrafluoroethylene (PTFE) are fitted into the two through-holes 708 in the flow channel member 702, and the tubes 718 made of perfluoroalkoxy alkanes (PFA) are connected to these joints 717 (see FIG. 15B). One of the tubes 718 is connected to the ozone water feed pump 616, and the other one of the tubes 718 is connected to the UFB-contained liquid collecting reservoir 604 (see FIG. 13).

The aluminum heat dissipation plate 711 is attached to the back surface of the support substrate 706 with a thermally conductive adhesive. Instead of the heat dissipation plate 711, a Peltier device or a water-cooling member may be placed. The UFB generating head 601 of the present embodiment is thus completed.

In the UFB generating head 601, the liquid flow channel 713 that connects to the two tubes 718 is formed between the flow channel member 702 and the element substrate 701. Then, ozone water supplied from one of the tubes 718 flows into the liquid flow channel 713 through one joint 717 and flows out through the other joint 717. The heating elements 700 are arranged in the liquid flow channel 713, and voltage is applied to each of the heating elements 700 at predetermined timing. Thereby, film boiling occurs in the ozone water in contact with each heating element 700, and ozone UFBs are generated due to generation, expansion, contraction, and collapse of film-boiling bubbles, according to the mechanism depicted in FIGS. 7A to 11B.

FIGS. 22A and 22B are diagrams showing the results of comparison about degrees of corrosion and deterioration caused by contact with ozone water in the above-described system that circulates ozone water. The comparison was made by the inventors of the present invention to select suitable materials for the units. FIGS. 22A and 22B show Groups A, B, and C. Group A is a group of materials in which almost no corrosion and deterioration were observed. Group B is a group of materials in which corrosion and deterioration were observed, but which were determined to be usable under predetermined conditions. Group C is a group of materials that came off due to corrosion and deterioration and were mixed into the ozone UFB-contained liquid as impurities.

The liquid flow channel 713 of the present embodiment is surrounded by a region of the element substrate 701 covered with an anti-cavitation film such as tantalum, iridium, or titanium, the flow channel member 702 made of stainless steel (SUS 316), and the seal member 712 made of PTFE. The substrate-side electrodes 715 electrically connected to the wiring substrate 703 is placed at a position outside the liquid flow channel 713 where the substrate-side electrodes 715 do not come into contact with ozone water. The tubes 718 that connect to the liquid flow channel 713 are made of PFA, and the joints 717 that connect to the tubes 718 are made of PTFE. Thus, in the UFB generating apparatus 1000 of the present embodiment, the materials of liquid contact portions that come into contact with ozone water are all made of materials included in Group A in FIG. 22. Thus, using the UFB generating apparatus 1000 of the present embodiment makes it possible to perform continuous operation and manufacture an ozone UFB-contained liquid with high purity and quality.

Second Embodiment

A second embodiment uses the UFB generating apparatus 1000 depicted in FIG. 13 as well.

Figure 16:
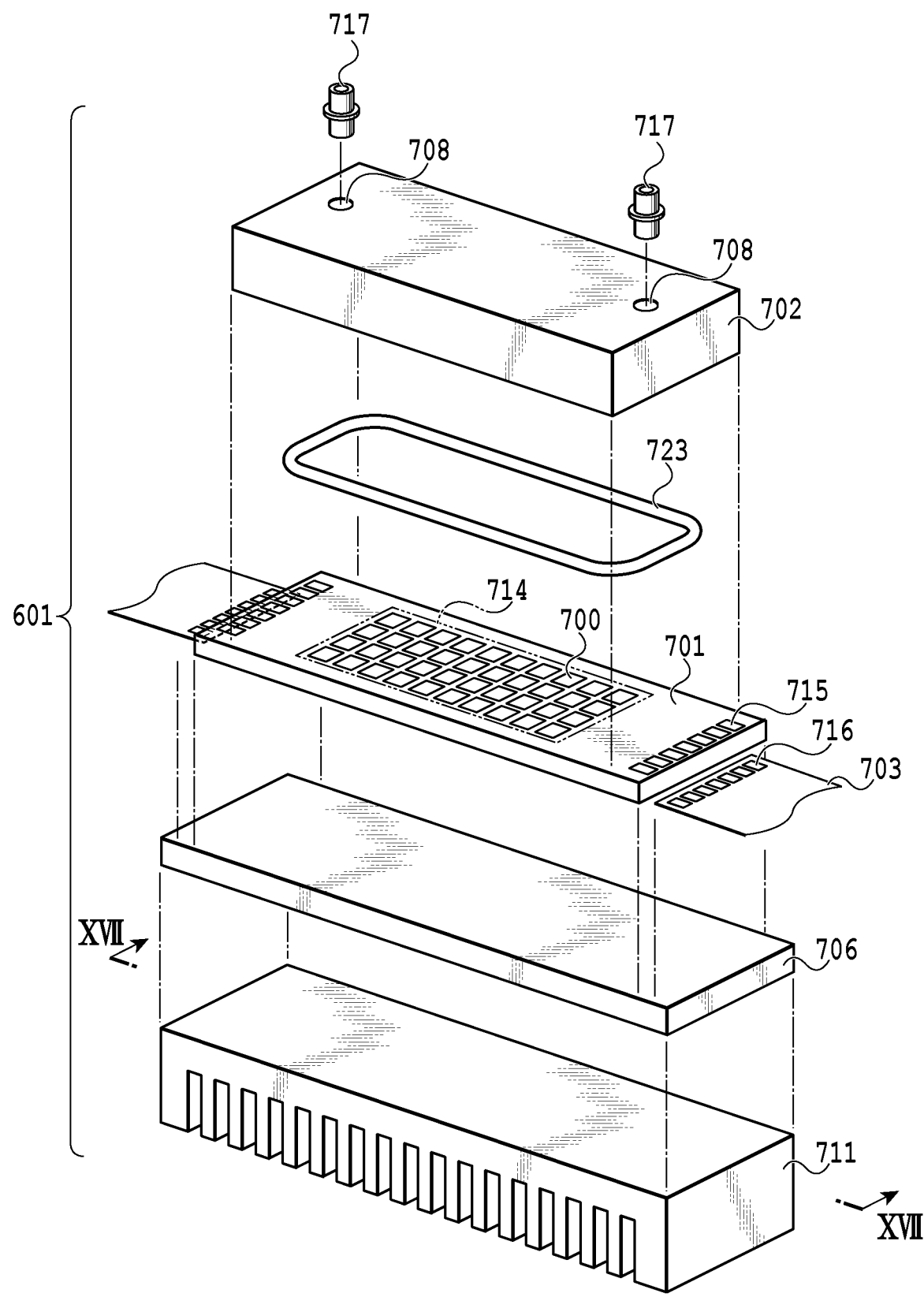
FIG. 16 is an exploded perspective view of a UFB generating head of a second embodiment.
Figure 17A:
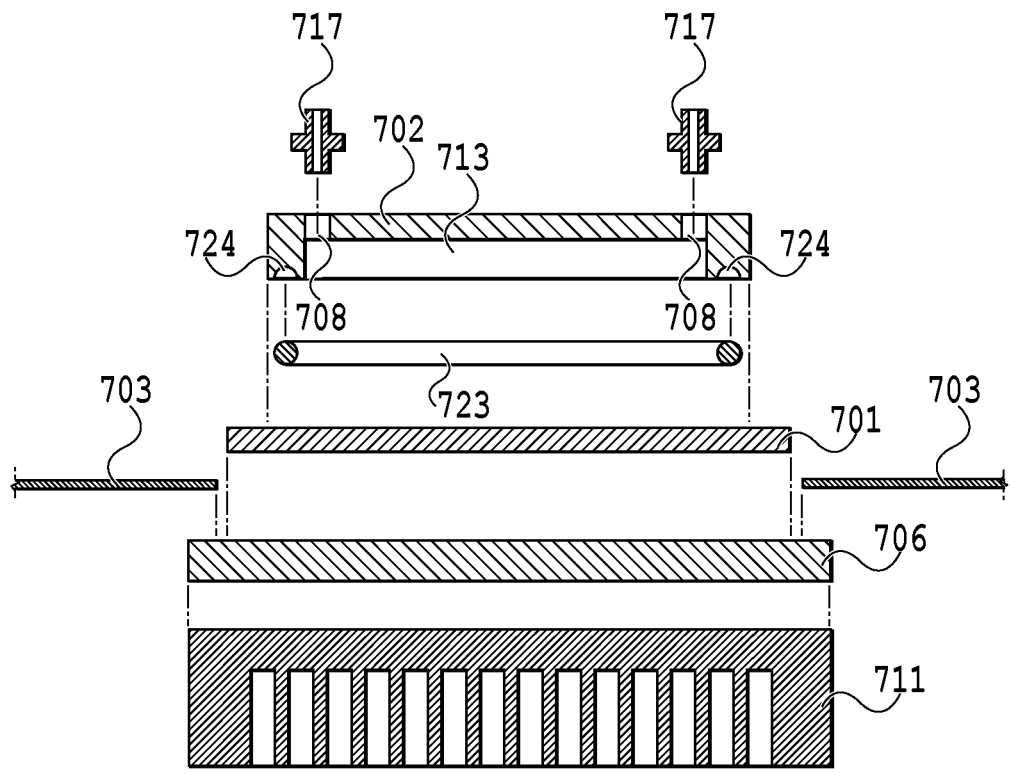
FIGS. 17A and 17B are sectional views of the UFB generating head of the second embodiment.
Figure 17B:
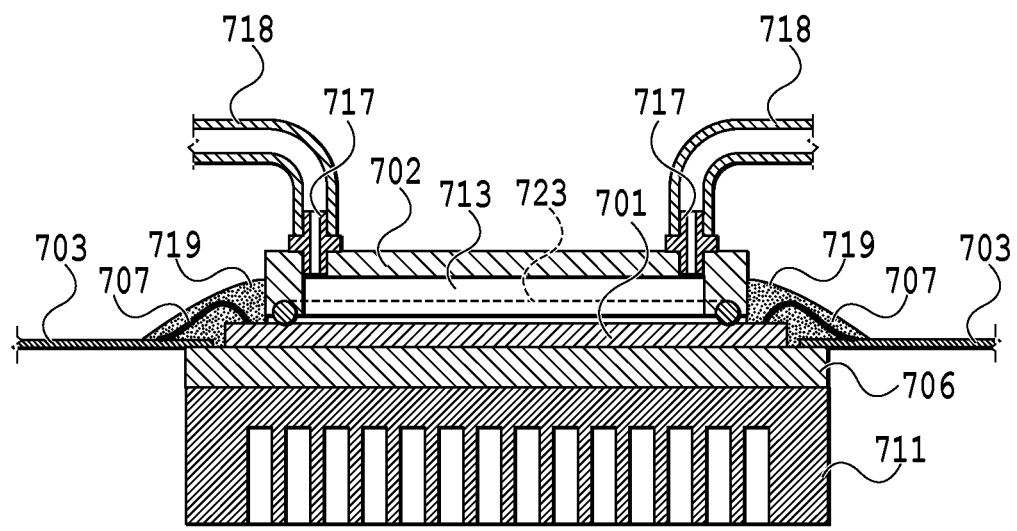

FIG. 16 is an exploded perspective view illustrating the configuration of the UFB generating head 601 used in the present embodiment. FIG. 17A is a sectional view of FIG. 16, and FIG. 17B is a sectional view of the UFB generating head 601.

The present embodiment differs from the first embodiment in that the seal member 712 is replaced by an O-ring 723. The O-ring 723 is made of vinylidene fluoride rubber (FKM; Viton (product name) manufactured by The Chemours Company), which is a fluororubber, and this is also one of the materials in Group A in FIGS. 22A and 22B.

In the formation of the flow channel member 702, a groove 724 is formed in the flow channel member 702 in advance for the O-ring 723 to be fitted thereinto. Then, in the manufacturing of the UFB generating head 601, the O-ring 723 is fitted into the groove 724 in the flow channel member 702, and then the flow channel member 702 is mounted onto the support substrate 706. With the flow channel member 702 being fixed to the support substrate 706 using a clamping jig (not shown), the cold-setting silicone sealer 719 is applied to the outer circumference of the flow channel member 702. The clamping jig is removed after the flow channel member 702 is confirmed to be bonded.

Also in the UFB generating head 601 of the present embodiment, the liquid flow channel 713 is surrounded by a material with excellent corrosion resistance to ozone water. The units other than the UFB generating head 601 are formed with materials with excellent oxidation resistance, like in the first embodiment. Thus, the UFB generating apparatus 1000 of the present embodiment too can operate continuously and manufacture an ozone UFB-contained liquid with high purity and quality.

Third Embodiment

A third embodiment uses the UFB generating apparatus 1000 depicted in FIG. 13 as well.

Figure 18A:
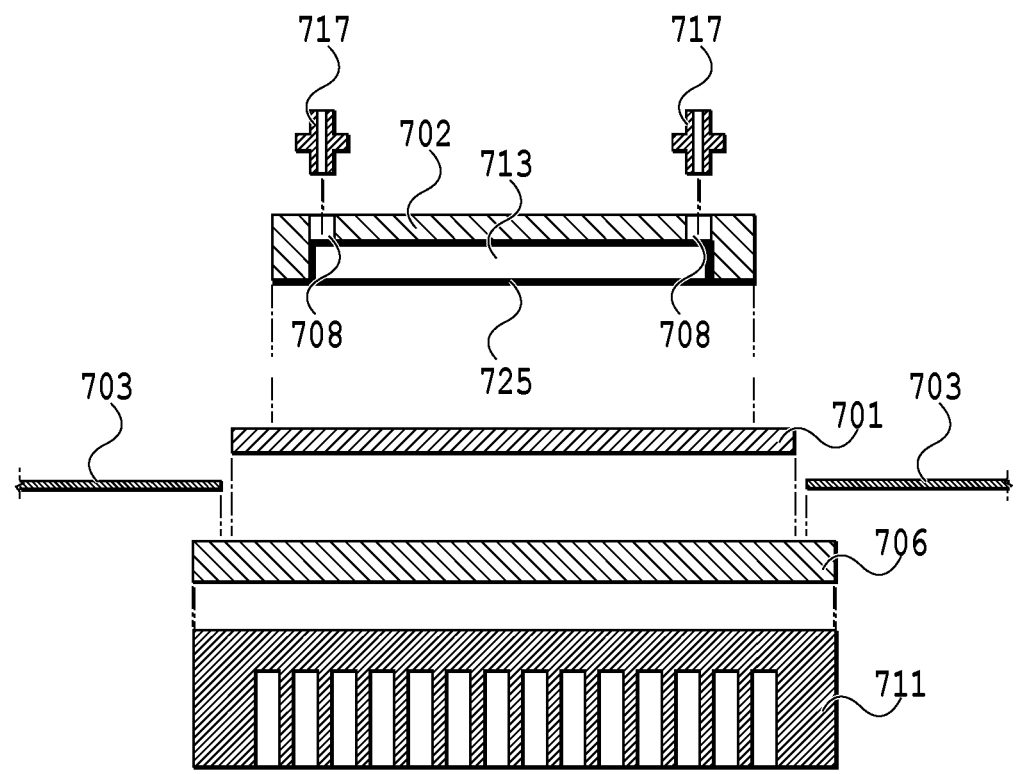
FIGS. 18A and 18B are sectional views of a UFB generating head of a third embodiment.
Figure 18B:
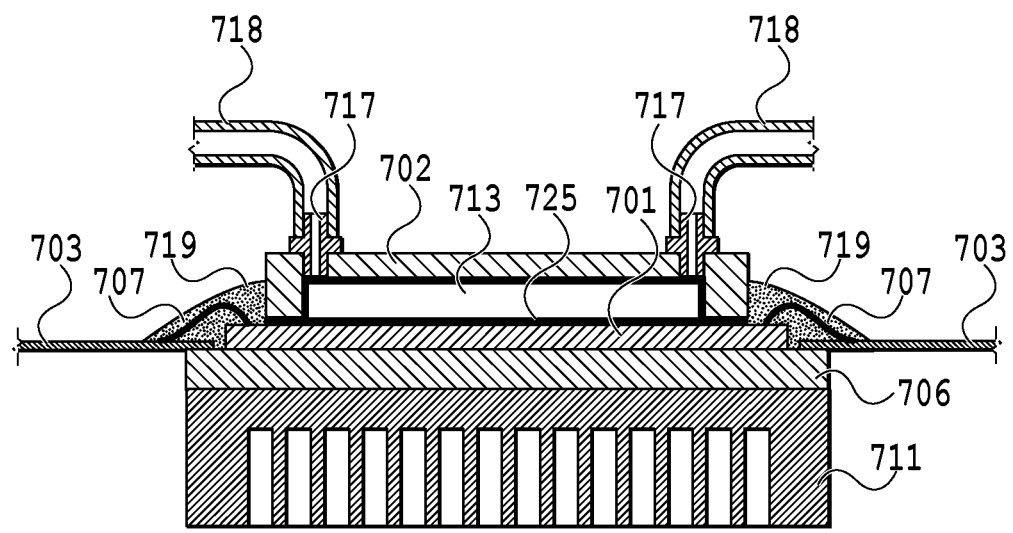

FIGS. 18A and 18B are diagrams illustrating the configuration of the UFB generating head 601 used in the present embodiment. FIG. 18A is an exploded sectional view of the UFB generating head 601, and FIG. 18B is a sectional view of the UFB generating head 601.

The present embodiment differs from the above embodiments in that neither the seal member 712 nor the O-ring 723 is used, and that the inner walls of the liquid flow channel 713 are coated with a fluororesin.

In the present embodiment, in the machining of the flow channel member 702 using stainless steel (SUS 316), the surface of the stainless steel (SUS 316) is roughened by sandblasting and is further subjected to a primer treatment. Thereafter, a fluororesin (PTFE) is sprayed onto the treated surface, which is then calcined to form a resin film 725. The thickness of the resin film 725 is 0.05 mm to 0.3 mm. To minimize the nonuniformity of film thickness due to liquid pooling along ridge lines, the irregularity of the surface of the resin film 725 is preferably within the range of 0.05 mm to 0.1 mm. However, such thickness and irregularity may be appropriately set according to the flow channel volume of the liquid flow channel 713 and the element substrate 701. Then, the stainless steel on which such a resin film 725 is formed is further machined to form the flow channel member 702.

Next, the flow channel member 702 is mounted onto the element substrate 701. Then, with the element substrate 701, the support substrate 706, and the flow channel member 702 being fixed to each other using a clamping jig (not shown), the cold-setting silicone sealer 719 is applied to the outer circumference of the flow channel member 702. The clamping jig is removed after the flow channel member 702 is confirmed to be bonded.

Coating the inner walls of the liquid flow channel 713 with a fluororesin also can help prevent damage to the surface of the element substrate 701 and prevent the silicone sealer 719 from being exposed to the liquid flow channel 713. Such a liquid flow channel 713 is also surrounded by a material with excellent corrosion resistance to ozone water. Thus, the UFB generating apparatus 1000 of the present embodiment also can operate continuously and manufacture an ozone UFB-contained liquid with high purity and quality.

In a case where the inner walls of the liquid flow channel 713 are coated with a fluororesin like in the present embodiment, the uncoated surfaces of the flow channel member 702 are not exposed to ozone water. Thus, the flow channel member 702 does not necessarily have to be made of a material with corrosion resistance to ozone water. In other words, according to the present embodiment, materials with somewhat lower corrosion resistance, such as the ones in Group B or C in FIGS. 22A and 22B, may become a possible candidate to be used for the flow channel member 702 of the present embodiment.

Fourth Embodiment

A fourth embodiment uses the UFB generating apparatus 1000 depicted in FIG. 13 as well. In the present embodiment, a plurality of element substrates 701 described in the first embodiment are arranged in the UFB generating head 601.

Figure 19:
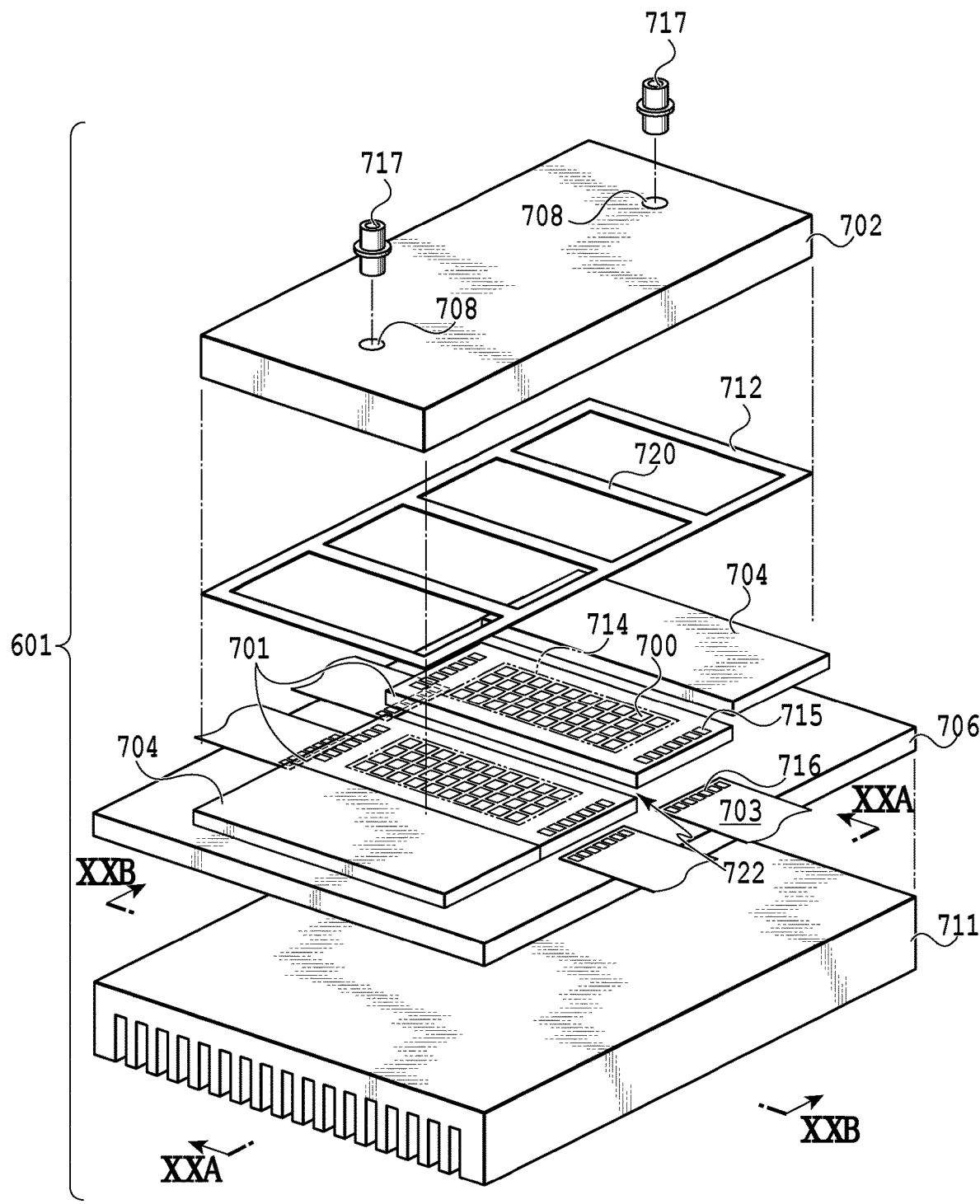
FIG. 19 is an exploded perspective view of a UFB generating head of a fourth embodiment.

FIG. 19 is an exploded perspective view illustrating the configuration of the UFB generating head 601 used in the present embodiment. FIGS. 20A and 20B are sectional views of the UFB generating head 601 taken in the longitudinal direction and the transverse direction, respectively.

In the manufacturing of the UFB generating head 601 of the present embodiment, two element substrates 701 are arranged side by side on and bonded to the alumina support substrate 706, and the wiring substrates 703 are connected to the element substrates 701. Next, height adjustment substrates 704 are bonded to the support substrate 706 at both sides of the set of two element substrates 701, forming a smooth surface continuous with the element substrates 701. The height adjustment substrates 704 are silicon substrates having a silicon oxide film formed on their surfaces. The positions where the height adjustment substrates 704 are placed correspond to the positions of the through-holes 708 that serve as the inflow and outflow ports for ozone water. Placing substrates that do not have heating elements at positions corresponding to the positions of the through-holes 708 can stabilize generation and contraction of film-boiling bubbles in the generation of UFBs in the liquid flow channel 713.

In a case where a plurality of substrates are arranged like in the present embodiment, a gap 722 which is several micrometers to several tens of micrometers may be generated in a border between adjacent substrates as shown in FIG. 20A. Then, bonding these substrates to the support substrate 706 with such a gap 722 generated therebetween may result in that an adhesive (a thermosetting epoxy adhesive) enters the gap 722. Then, flowing of ozone water into the liquid flow channel 713 in such a state causes the adhesive to corrode or decompose, consequently degrading the purity of the ozone UFB-contained liquid.

To avoid this, the present embodiment employs the seal member 712 which is provided in advance with seal member crosspieces 720 at positions corresponding to the positions of the gaps 722. In addition, the flow channel member 702 in the present embodiment also is provided in advance with flow channel member crosspieces 721 on its inner walls, at positions corresponding to the positions of the gaps 722. Then, after the seal member 712 is positioned relative to the support substrate 706 so that the seal member crosspieces 720 may cover the gaps 722, the flow channel member 702 is mounted with this seal member 712 interposed. Then, with the element substrate 701, the support substrate 706, and the flow channel member 702 fixed to each other using a clamping jig (not shown), the cold-setting silicone sealer 719 is applied to the outer circumference of the flow channel member 702. As a result, the element substrate 701 and the flow channel member 702 are fixed together with the gaps 722 being sealed by the seal member crosspieces 720 pressed against the flow channel member crosspieces 721. Consequently, the liquid flow channel 713 thus formed is surrounded by a material with excellent corrosion resistance to ozone water.

FIGS. 21A to 21D are diagrams illustrating how to fabricate the flow channel member 702 including the flow channel member crosspieces 721. The flow channel member 702 of the present embodiment is fabricated by stacking a first layer 702A, a second layer 702B, and a third layer 702C in this order.

Figure 21A:
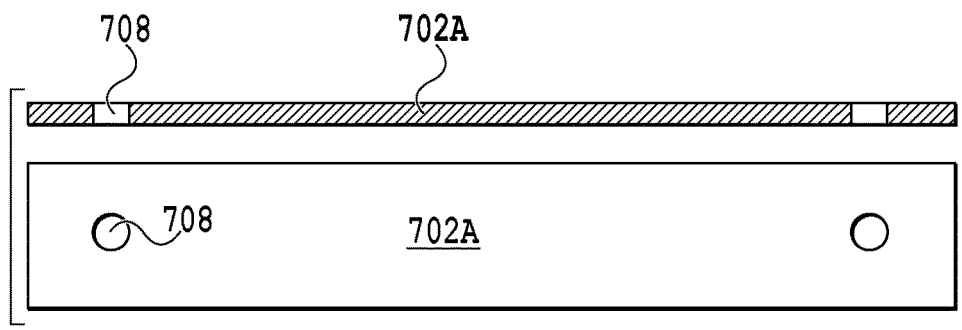
FIGS. 21A to 21D are diagrams illustrating how to fabricate a flow channel member of the fourth embodiment.

FIG. 21A is a sectional view and a top view of the first layer 702A which is the top plate of the flow channel member 702. The first layer 702A is a smooth, flat plate and has two through-holes 708 formed at both ends in the longitudinal direction, which serve as inflow and outflow ports for ozone water.

Figure 21B:
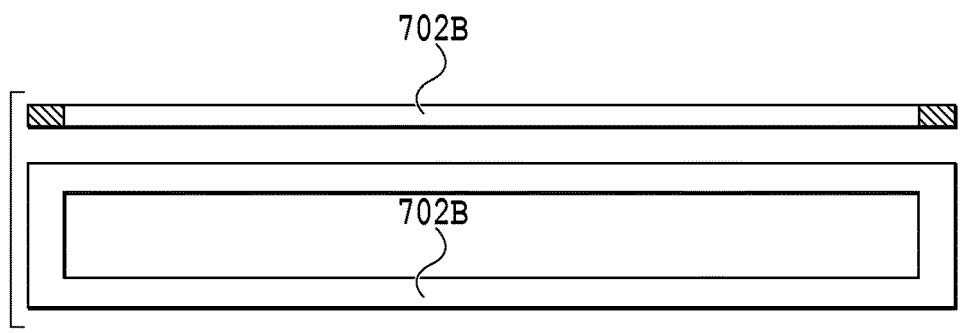

FIG. 21B is a sectional view and a top view of the second layer 702B. The second layer 702B corresponds to an outer frame that supports the first layer 702A of the flow channel member 702.

Figure 21C:
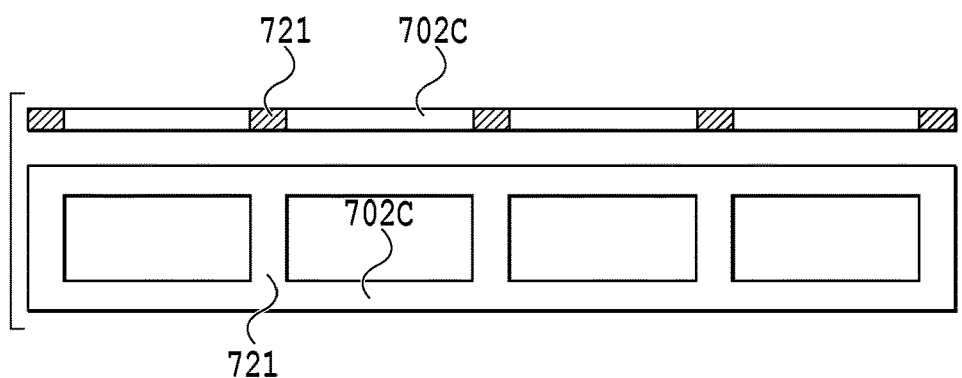

FIG. 21C is a sectional view and a top view of the third layer 702C. The third layer 702C includes a frame portion that supports the second layer 702B and the flow channel member crosspieces 721 placed at positions corresponding to the positions of the gaps 722.

In the present embodiment, processes such as a laser process, wire cutting, and etching are performed on a plate member which is made of SUS 316 and 0.1 mm to 1 mm thick to form the first layer 702A, the second layer 702B, and the third layer 702C without causing twist and warpage.

Figure 21D:
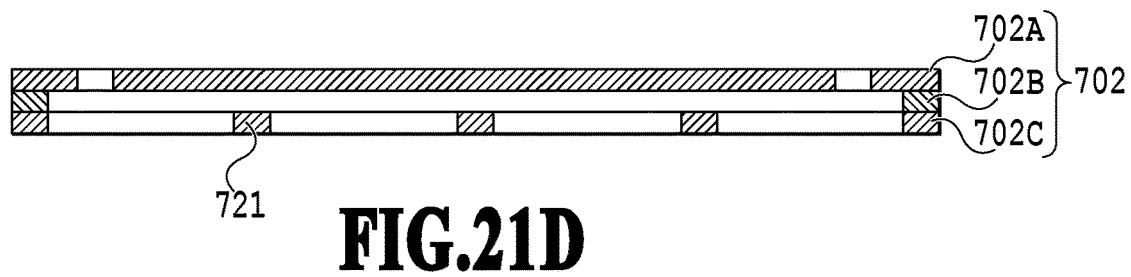

FIG. 21D is a sectional view of the flow channel member 702 fabricated by attachment of the first layer 702A, the second layer 702B, and the third layer 702C. For this attachment, diffusion bonding was employed to bond the members together, considering that the element substrate 701 is flat on the flow channel member 702 side, no liquid leaks from gaps in the stack, and the adhesive used for the attachment does not come into contact with ozone water.

The liquid flow channel 713 in the UFB generating head 601 of the present embodiment described above also is surrounded by a material with excellent corrosion resistance to ozone water. Liquid contact portions in the units other than the UFB generating head 601 which come into contact with ozone water are also formed with materials with excellent oxidizing resistance like in the first embodiment. Thus, the UFB generating apparatus 1000 of the present embodiment also can operate continuously and manufacture an ozone UFB-contained liquid with high purity and quality.

Moreover, by increasing the number of element substrates arranged, the UFB generating head 601 of the present embodiment can generate more ozone UFBs per unit time than the UFB generating head 601 described in the first embodiment.

A brief description is given below of results of evaluation conducted by the inventors of the present invention using the UFB generating apparatus 1000 depicted in FIG. 13. In this evaluation, the element substrate 701 was prepared which measured 22 mm×17 mm and had 12,288 heating elements arranged thereon. With six such element substrates arranged in series, the UFB generating head was manufactured with the method of the fourth embodiment. The UFB generating head had a total of 73,728 heating elements.

With ozone water caused to flow in the liquid flow channel of the UFB generating head at a rate of 180 ml to 200 ml per minute, each of the 73,728 heating elements were driven at a drive frequency of 7.5 kHz. As a result, it was observed that approximately one billion ozone UFBs were generated per 1 ml. Further, with the UFB generating head continued to be driven, an ozone UFB-contained liquid was circulated. Thereby, a high-concentration ozone UFB-contained liquid which contains four to five billion ozone UFBs per 1 ml could be generated.

Fifth Embodiment

A fifth embodiment uses the UFB generating apparatus 1000 depicted in FIG. 13 as well. In the present embodiment, a plurality of element substrates 701 described in the first embodiment are arranged in the UFB generating head 601.

Figure 23:
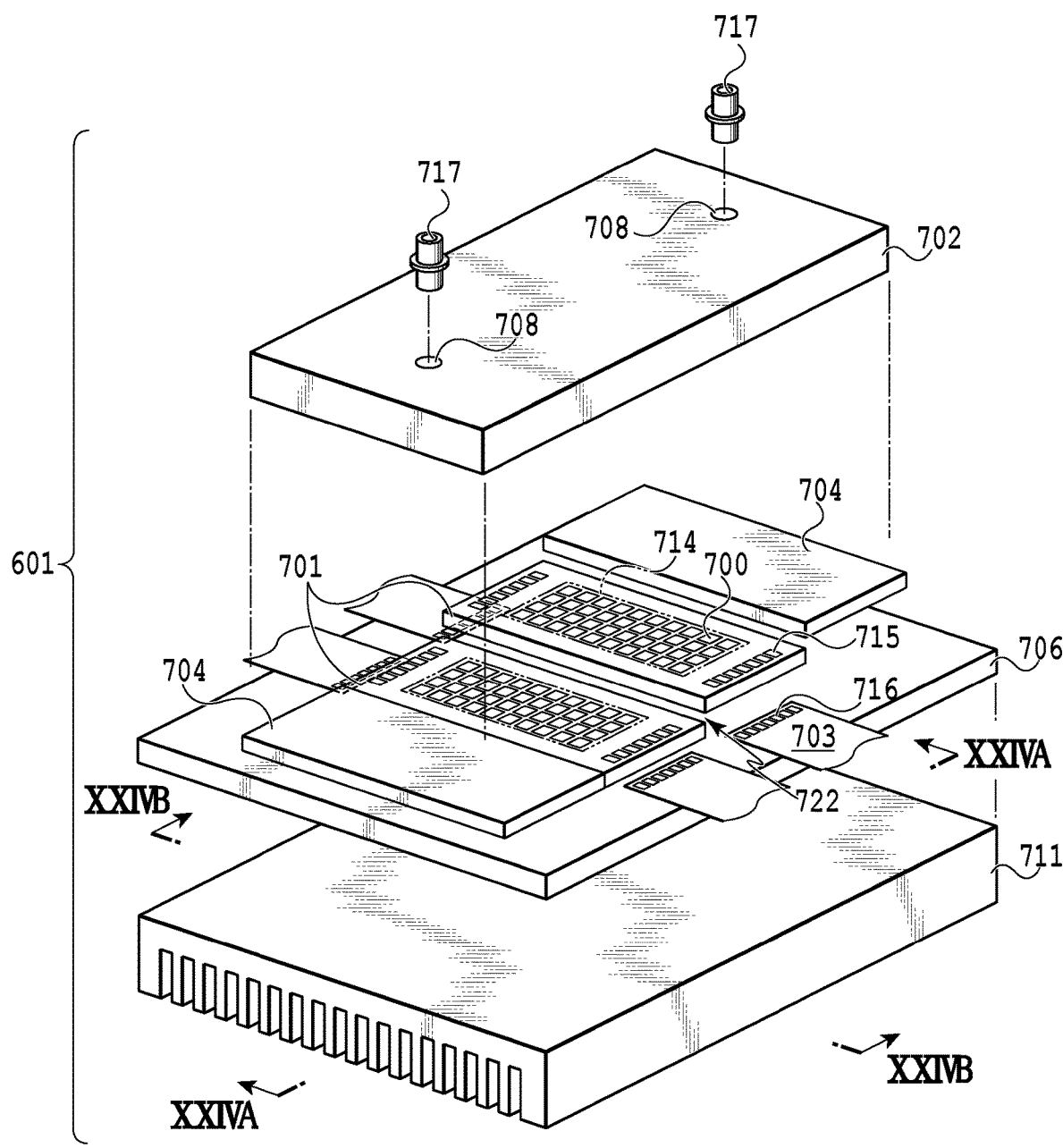
FIG. 23 is an exploded perspective view of a UFB generating head of a fifth embodiment.

FIG. 23 is an exploded perspective view illustrating the configuration of the UFB generating head 601 used in the present embodiment. FIGS. 24A and 24B are sectional views of the UFB generating head 601 taken in the longitudinal direction and the transverse direction, respectively. In the present embodiment, like in the fourth embodiment, in the manufacturing of the UFB generating head 601, two element substrates 701 are arranged side by side on and bonded to the alumina support substrate 706, and the wiring substrates 703 are connected to the element substrates 701. Next, the height adjustment substrates 704 are bonded to the support substrate 706 at both sides of the set of two element substrates 701, forming a smooth surface continuous with the element substrates 701. The height adjustment substrates 704 are silicon substrates having a silicon oxide film formed on their surfaces. The positions where the height adjustment substrates 704 are placed correspond to the positions of the through-holes 708 that serve as the inflow and outflow ports for ozone water. Placing substrates that do not have heating elements at positions corresponding to the positions of the through-holes 708 can stabilize generation and contraction of film-boiling bubbles in the generation of UFBs in the liquid flow channel 713.

In the present embodiment, a hardened material (fluororesin) of a liquid fluorinated elastomer (SIFEL2000 manufactured by Shin-Etsu Chemical Co., Ltd.) is used to bond the element substrates 701 and the height adjustment substrates 704 to the alumina support substrate 706. Using this adhesive can suppress degradation of the purity of the ozone UFB-contained liquid because the adhesive does not corrode or decompose even in a case where ozone water flows into the gap 722 generated between the element substrates. The present embodiment therefore does not need the seal member used in the above embodiment which is provided with the crosspieces to close the gaps. The flow channel member 702 and portions with gold wires 707 that connect the electrodes 715 on the element substrates 701 to the flexible wiring substrates 703 are covered with a hardened material of a liquid fluorinated elastomer 719 to protect against liquid leakage from the flow channel member and protect the gold wires. In particular, due to capillary force, the liquid fluorinated elastomer 719 applied to the periphery of the flow channel member flows into and fill the gaps 722 between the element substrates. Thus, the UFB generating head 601 does not need the seal member and has an extremely simple structure.

Sixth Embodiment

Figure 25:
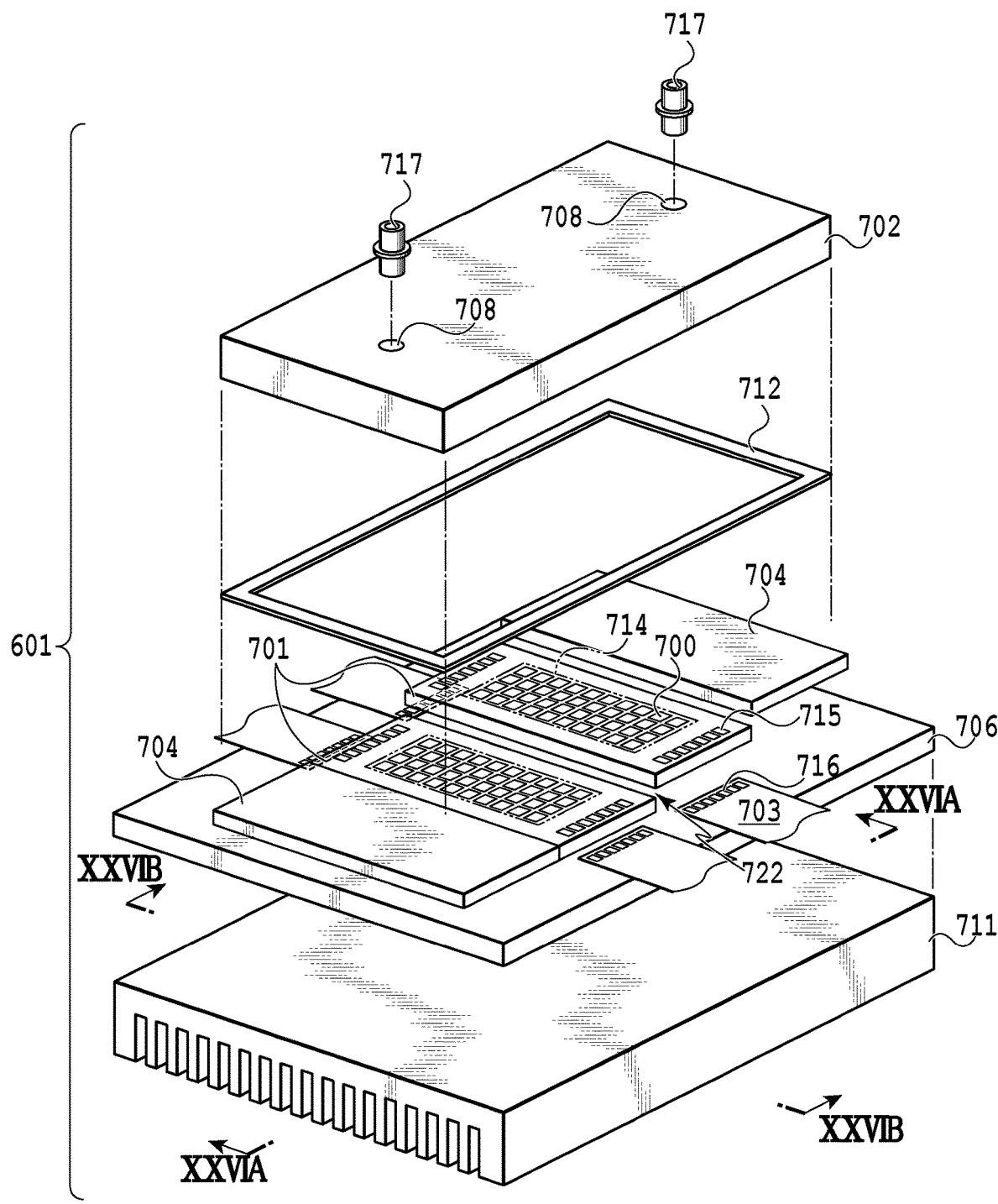
FIG. 25 is an exploded perspective view of a UFB generating head of a sixth embodiment.

A sixth embodiment includes the seal member 712 made of PTFE to avoid problems caused by placing the flow channel member 702 directly on the element substrates 701 in the fifth embodiment. FIG. 25 is an exploded perspective view illustrating the configuration of the UFB generating head 601 used in the present embodiment. FIGS. 26A and 26B are sectional views of the UFB generating head 601 taken in the longitudinal direction and the transverse direction, respectively.

The present embodiment does not need the crosspieces 720 of the seal member either because the gaps 722 between the element substrates are filled with a liquid fluorinated elastomer. The structure is simplified because the crosspieces 721 on the flow channel member side that are pressed against the crosspieces 720 are also unnecessary.

Other Embodiments

Although specific materials usable for the units in the first to sixth embodiments have been described, the materials may be changed as long as they are included in Group A in FIGS. 22A and 22B. For example, as a material for forming the support substrate 706, borosilicate glass (Pyrex (registered trademark)) may be used instead of alumina ceramics. It goes without saying that a material not included in Group A in FIGS. 22A and 22B may be used as long as the material has excellent oxidation resistance and is unlikely to corrode upon contact with ozone water.

For example, according to the evaluation conducted by the inventors of the present invention, even austenitic stainless steel included in Group B could be enhanced in its corrosion resistance by containing 0.08% or less of carbon, 16% to 18% of chromium, 10% to 15% of nickel, and 2% to 3% of molybdenum. Consequently, it was found that this material was usable for some of the units of the UFB generating apparatus, such as the flow channel member.

Although the elements-arranged area 714 and the substrate-side electrodes 715 for supplying power to the elements-arranged area 714 are formed on the same side of the element substrate 701 in the above embodiments, the substrate-side electrodes 715 may be formed on the back side of the element substrate 701. In this case, the wiring substrates 703 are wire-bonded to the back side of the element substrate 701. In this way, there is even less possibility that the portions where the substrate-side electrodes 715 are connected to the wiring substrate-side electrodes 716 come into contact with ozone water, which makes it possible to protect the electrodes from ozone water more reliably.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2020-021491, filed Feb. 12, 2020, and No. 2021-016052, filed Feb. 3, 2021, which are hereby incorporated by reference wherein in their entirety.

What is claimed is:

1. An ultrafine bubble generating apparatus capable of generating ultrafine bubbles containing ozone by causing film boiling in ozone water, wherein a liquid contact portion that comes into contact with the ozone water is made of a material with corrosion resistance to the ozone water,
   the apparatus comprising an ultrafine bubble generating head that includes:
   an element substrate on which a heating element is placed, the heating element generating heat upon application of voltage thereto and thereby causing the film boiling in the ozone water, and
   a flow channel member that forms a liquid flow channel which faces the element substrate and which contains the ozone water,
   wherein the element substrate and the flow channel member are bonded with a seal member made of a fluororesin interposed therebetween.

2. The ultrafine bubble generating apparatus according to claim 1, wherein the liquid contact portion is made of any one or a combination of a fluororesin, a fluororubber, titanium, tantalum, iridium, stainless steel, alumina ceramics, and borosilicate glass.

3. The ultrafine bubble generating apparatus according to claim 1, wherein the element substrate is a silicon substrate, wherein a surface of the silicon substrate that is to come into contact with the ozone water is covered with polytetrafluoroethylene, and
   wherein the flow channel member is made of stainless steel or borosilicate glass.

4. The ultrafine bubble generating apparatus according to claim 1, wherein the element substrate is a silicon substrate, wherein a surface of the silicon substrate that is to come into contact with the ozone water is covered with a material which is tantalum, iridium, titanium, or a combination thereof, and
   wherein the flow channel member is made of stainless steel or borosilicate glass.

5. The ultrafine bubble generating apparatus according to claim 3, wherein the flow channel member is made of SUS 316.

6. The ultrafine bubble generating apparatus according to claim 3, wherein the flow channel member is made of austenitic stainless steel containing carbon, chromium, nickel, and molybdenum.

7. The ultrafine bubble generating apparatus according to claim 1, wherein a plurality of the element substrates are arranged in the ultrafine bubble generating head,
  wherein the seal member is provided with a first crosspiece for sealing a border between the plurality of element substrates at a position corresponding to a position of the border, and
  wherein the flow channel member is provided with a second crosspiece at a position corresponding to the position of the border between the element substrates to press the first crosspiece toward the border.

8. The ultrafine bubble generating apparatus according to claim 1, wherein an inner wall of the flow channel member is coated with a fluororesin.

9. The ultrafine bubble generating apparatus according to claim 1, wherein the flow channel member includes an inflow port through which the ozone water flows into the liquid flow channel and an outflow port through which the ozone water flows out of the liquid flow channel, and
  wherein the inflow port and the outflow port are formed at positions that do not face a region where the heating element of the element substrate is placed.

10. The ultrafine bubble generating apparatus according to claim 9, wherein joints made of a fluororubber are connected to the inflow port and the outflow port.

11. The ultrafine bubble generating apparatus according to claim 1, wherein the element substrate includes an electrode to receive a signal for driving the heating element, the electrode being located at a position where the electrode does not come into contact with the ozone water contained in the liquid flow channel.

12. The ultrafine bubble generating apparatus according to claim 11, wherein the electrode is placed on a surface of the element substrate to which the flow channel member is bonded, at a position outside the flow channel member.

13. The ultrafine bubble generating apparatus according to claim 11, wherein the electrode is placed on a surface of the element substrate opposite from a surface to which the flow channel member is bonded.

14. The ultrafine bubble generating apparatus according to claim 1, further comprising a circulation flow channel capable of circulating the ozone water between the ultrafine bubble generating head and at least one unit.

15. An ultrafine bubble generating apparatus capable of generating ultrafine bubbles containing ozone by causing film boiling in ozone water, wherein a liquid contact portion that comes into contact with the ozone water is made of a material with corrosion resistance to the ozone water,
  the apparatus comprising an ultrafine bubble generating head that includes:
  an element substrate on which a heating element is placed, the heating element generating heat upon application of voltage thereto and thereby causing the film boiling in the ozone water, and
  a flow channel member that forms a liquid flow channel which faces the element substrate and which contains the ozone water,
  wherein the element substrate and the flow channel member are bonded to each other with an O-ring made of a fluororubber interposed therebetween.

16. The ultrafine bubble generating apparatus according to claim 15, wherein the liquid contact portion is made of any one or a combination of a fluororesin, a fluororubber, titanium, tantalum, iridium, stainless steel, alumina ceramics, and borosilicate glass.

17. The ultrafine bubble generating apparatus according to claim 15, wherein the element substrate is a silicon substrate,
  wherein a surface of the silicon substrate that is to come into contact with the ozone water is covered with polytetrafluoroethylene, and
  wherein the flow channel member is made of stainless steel or borosilicate glass.

18. The ultrafine bubble generating apparatus according to claim 15, wherein the element substrate is a silicon substrate,
  wherein a surface of the silicon substrate that is to come into contact with the ozone water is covered with a material which is tantalum, iridium, titanium, or a combination thereof, and
  wherein the flow channel member is made of stainless steel or borosilicate glass.

19. The ultrafine bubble generating apparatus according to claim 17, wherein the flow channel member is made of SUS 316.

20. The ultrafine bubble generating apparatus according to claim 17, wherein the flow channel member is made of austenitic stainless steel containing carbon, chromium, nickel, and molybdenum.

21. The ultrafine bubble generating apparatus according to claim 15, wherein an inner wall of the flow channel member is coated with a fluororesin.

22. The ultrafine bubble generating apparatus according to claim 15, wherein the flow channel member includes an inflow port through which the ozone water flows into the liquid flow channel and an outflow port through which the ozone water flows out of the liquid flow channel, and
  wherein the inflow port and the outflow port are formed at positions that do not face a region where the heating element of the element substrate is placed.

23. The ultrafine bubble generating apparatus according to claim 22, wherein joints made of a fluororubber are connected to the inflow port and the outflow port.

24. The ultrafine bubble generating apparatus according to claim 15, wherein the element substrate includes an electrode to receive a signal for driving the heating element, the electrode being located at a position where the electrode does not come into contact with the ozone water contained in the liquid flow channel.

25. The ultrafine bubble generating apparatus according to claim 24, wherein the electrode is placed on a surface of the element substrate to which the flow channel member is bonded, at a position outside the flow channel member.

26. The ultrafine bubble generating apparatus according to claim 24, wherein the electrode is placed on a surface of the element substrate opposite from a surface to which the flow channel member is bonded.

27. The ultrafine bubble generating apparatus according to claim 15, further comprising a circulation flow channel capable of circulating the ozone water between the ultrafine bubble generating head and at least one unit.

* * * * *